United States Patent
Sharma et al.

(10) Patent No.: US 12,390,090 B2
(45) Date of Patent: Aug. 19, 2025

(54) MEDICAL DEVICE WITH MULTIPLE DEGREES OF FREEDOM AND RELATED METHODS

(71) Applicant: Boston Scientific Medical Device Limited, Galway (IE)

(72) Inventors: Deepak Kumar Sharma, Muzaffarnagar (IN); Nabarun Bhowmick, Kolkata (IN); Shrikant Vasant Raut, Mumbai (IN); Sharath Kumar G, Kanakapura (IN); James J. Scutti, Norwell, MA (US); Juan Pablo Ortiz Garcia, Heredia (CR)

(73) Assignee: Boston Scientific Medical Device Limited, Galway (IE)

( * ) Notice: Subject to any disclaimer, the term of this patent is extended or adjusted under 35 U.S.C. 154(b) by 541 days.

(21) Appl. No.: 17/783,932

(22) PCT Filed: Dec. 8, 2020

(86) PCT No.: PCT/IB2020/001038
§ 371 (c)(1),
(2) Date: Jun. 9, 2022

(87) PCT Pub. No.: WO2021/116767
PCT Pub. Date: Jun. 17, 2021

(65) Prior Publication Data
US 2023/0010697 A1 Jan. 12, 2023

Related U.S. Application Data

(60) Provisional application No. 62/946,483, filed on Dec. 11, 2019.

(51) Int. Cl.
*A61B 17/00* (2006.01)
*A61B 1/00* (2006.01)
(Continued)

(52) U.S. Cl.
CPC ...... *A61B 1/00066* (2013.01); *A61B 1/00087* (2013.01); *A61B 1/0052* (2013.01); *A61B 1/0057* (2013.01)

(58) Field of Classification Search
CPC ............ A61B 1/00066; A61B 1/00087; A61B 1/0052; A61B 1/0055; A61B 1/0057;
(Continued)

(56) References Cited

U.S. PATENT DOCUMENTS

| | | |
|---|---|---|
| 5,374,277 A | 12/1994 | Hassler |
| 9,226,767 B2 | 1/2016 | Stulen et al. |

(Continued)

FOREIGN PATENT DOCUMENTS

| | | |
|---|---|---|
| EP | 2316366 A2 | 5/2011 |
| JP | 2011-92743 A | 5/2011 |
| JP | 2014-513561 A | 6/2014 |

OTHER PUBLICATIONS

International Search Report and Written Opinion issued on Mar. 26, 2021, in counterpart International Patent Application No. PCT/IB2020/001038 (13 pages, in English).

*Primary Examiner* — Khadijeh A Vahdat
(74) *Attorney, Agent, or Firm* — Bookoff McAndrews, PLLC

(57) ABSTRACT

A medical device having multiple degrees of freedom independent of each other. The medical device includes a handle, an end effector, and a tubular section extending between the handle and the end effector. The end effector is configured to be rotated about a first axis extending through the tubular section without rotating the tubular section. And, the tubular section is configured to be rotated about the first axis with the end effector.

9 Claims, 18 Drawing Sheets

(51) Int. Cl.
*A61B 1/005* (2006.01)
*A61B 18/14* (2006.01)

(58) Field of Classification Search
CPC ....... A61B 1/2676; A61B 1/2736; A61B 1/31;
A61B 18/1492; A61B 2017/00309; A61B
2017/00327; A61B 2018/00577; A61B
2018/00601; A61B 2018/1412; A61M
25/0136; A61M 25/0138; A61M 25/0147
See application file for complete search history.

(56) References Cited

U.S. PATENT DOCUMENTS

| | | |
|---|---|---|
| 10,617,438 B2 | 4/2020 | O'Keefe et al. |
| 2005/0043758 A1 | 2/2005 | Golden et al. |
| 2009/0299143 A1 | 12/2009 | Conlon et al. |
| 2010/0249497 A1 | 9/2010 | Peine et al. |
| 2011/0106073 A1 | 5/2011 | Mueller |
| 2013/0296878 A1 | 11/2013 | Shin |
| 2015/0250530 A1* | 9/2015 | Manzo ............... A61B 18/1482 606/51 |
| 2016/0192999 A1 | 7/2016 | Stulen et al. |
| 2018/0132923 A1 | 5/2018 | Simani et al. |

* cited by examiner

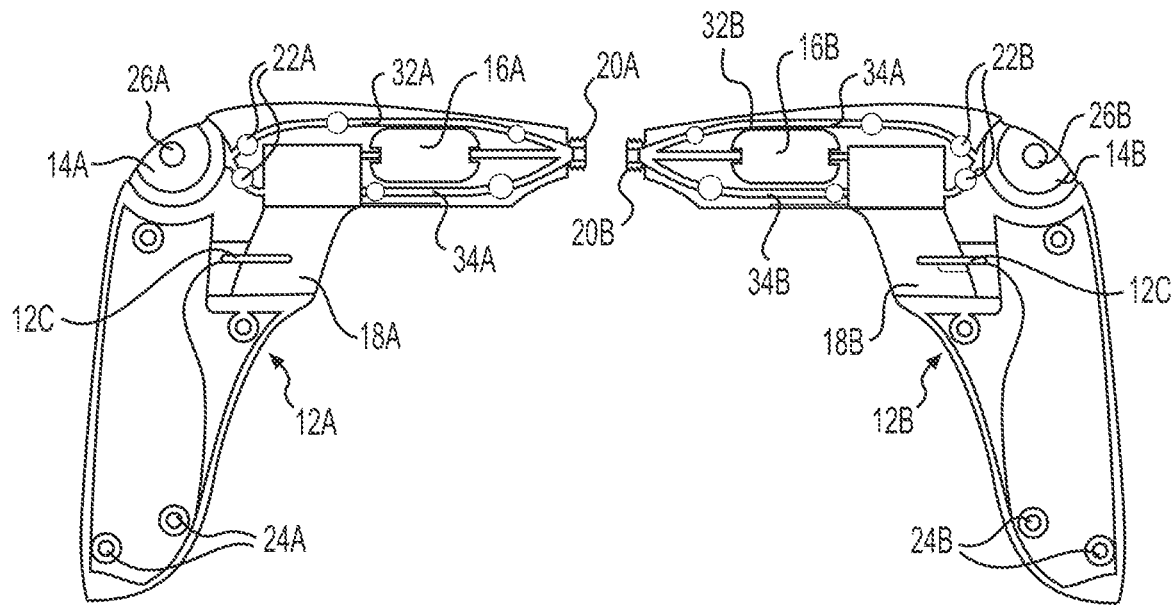
FIG. 3B  FIG. 3C
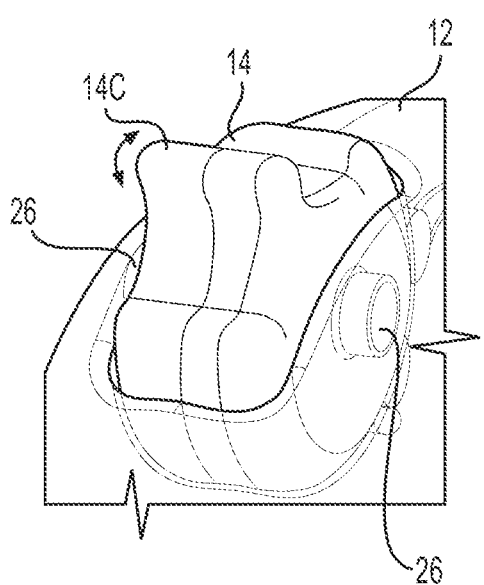  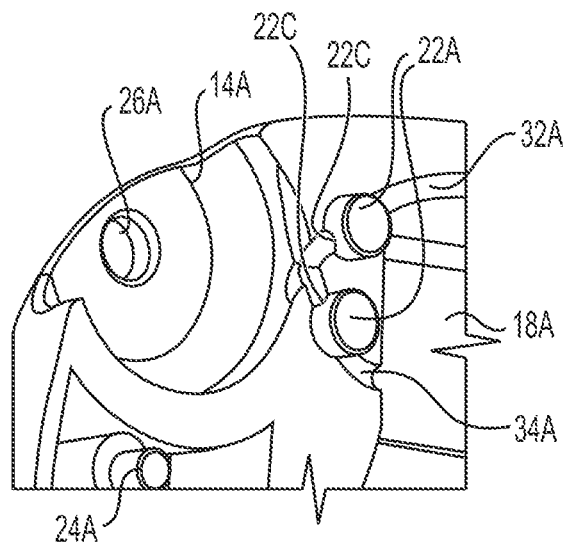
FIG. 4A  FIG. 4B

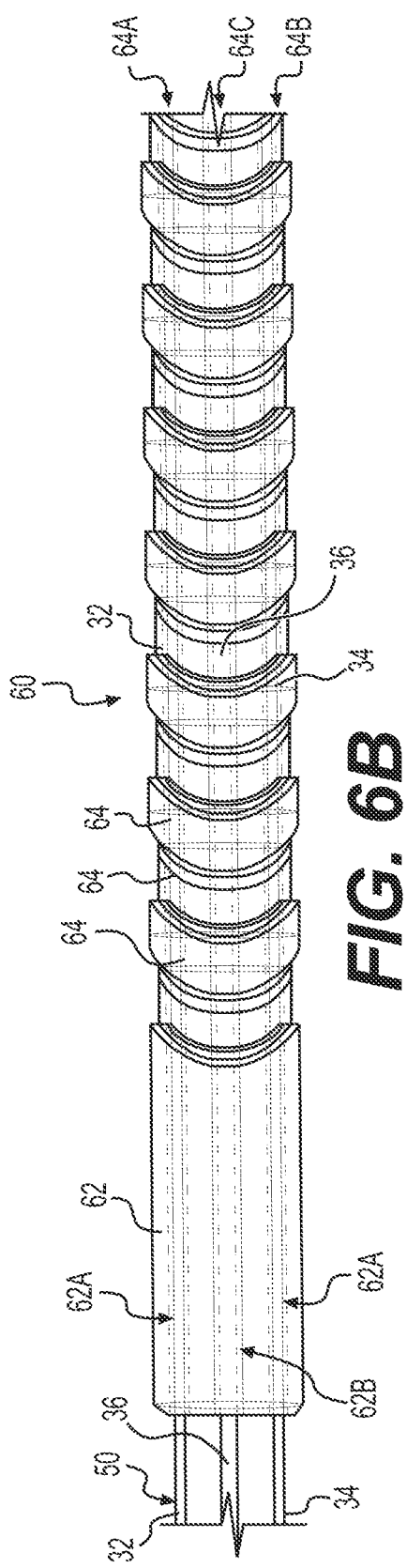
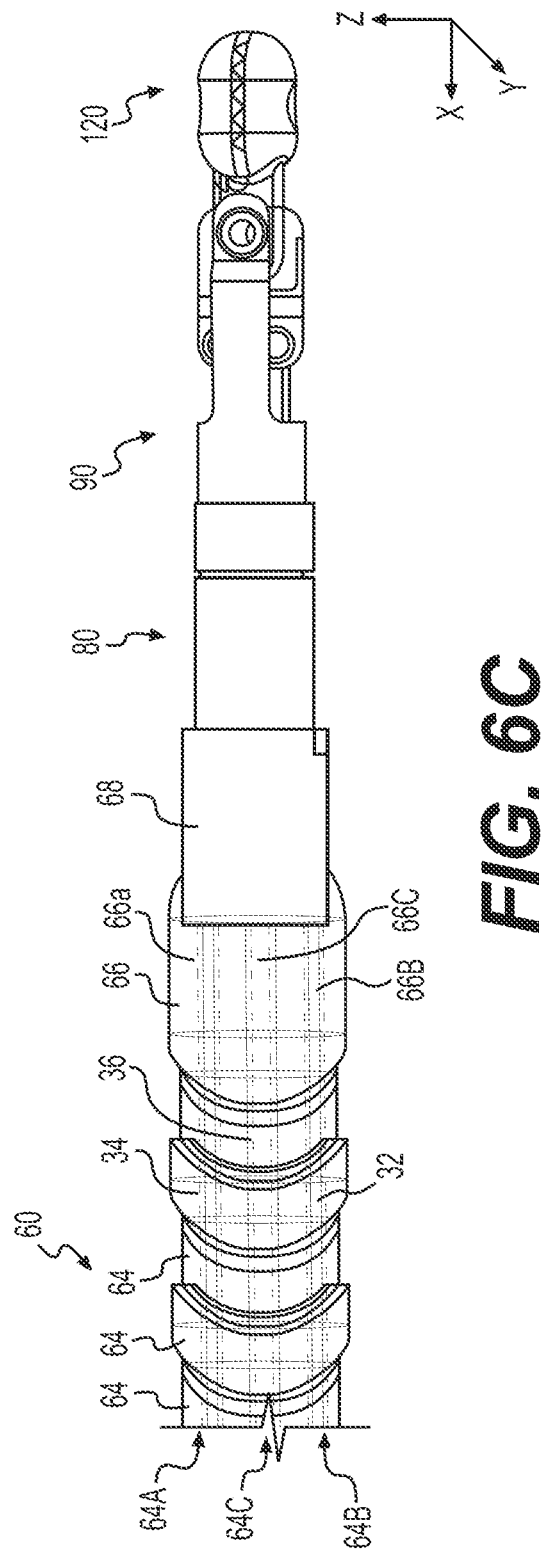
FIG. 6B
FIG. 6C

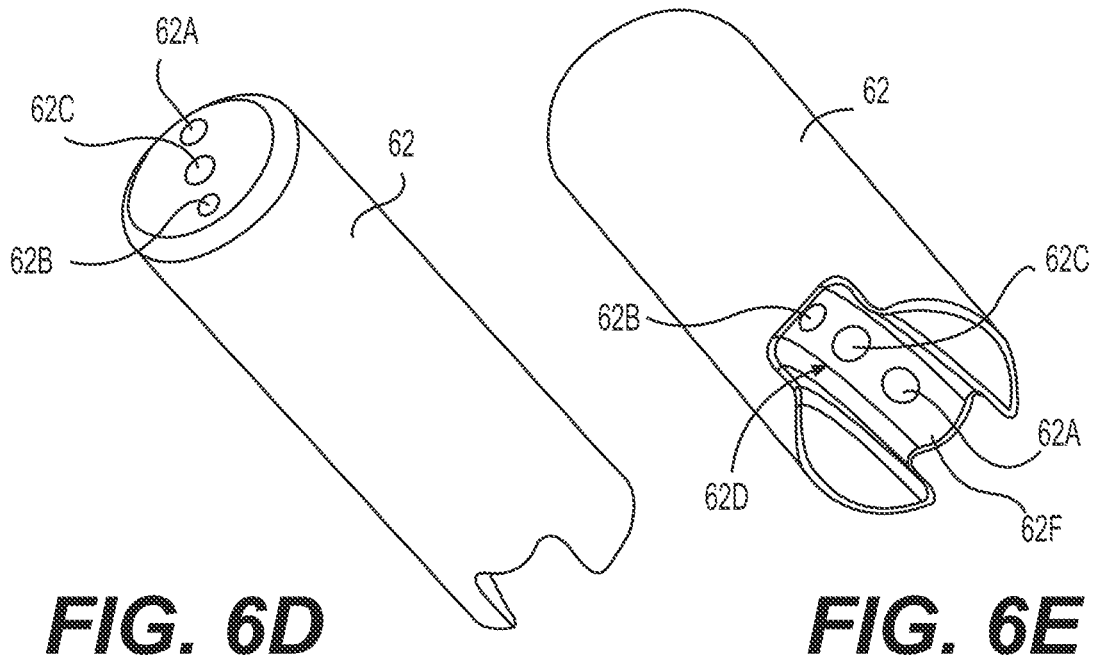
*FIG. 6D*   *FIG. 6E*
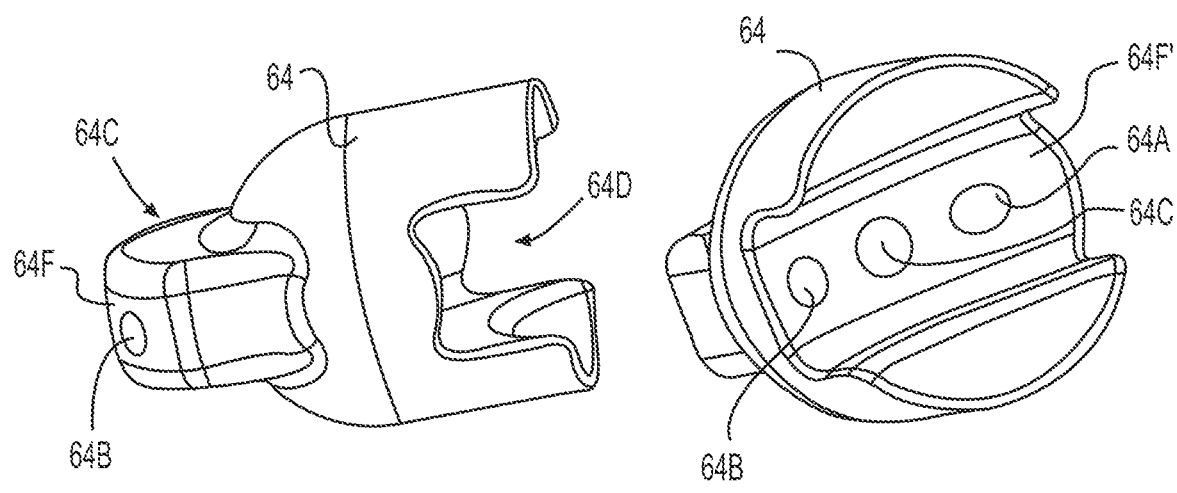
*FIG. 6F*   *FIG. 6G*

MEDICAL DEVICE WITH MULTIPLE DEGREES OF FREEDOM AND RELATED METHODS

This application is a § 371 National Stage Application of pending International Application No. PCT/IB2020/001038, filed Dec. 8, 2020, which claims the benefit of priority from U.S. Provisional Application No. 62/946,483, filed Dec. 11, 2019, each of which is incorporated by reference herein in its entirety.

TECHNICAL FIELD

Various aspects of this disclosure generally relate to medical devices for manipulating and/or treating tissue during a procedure. In particular, aspects of this disclosure relate to medical devices having multiple degrees of freedom and methods for performing a procedure using the disclosed devices.

BACKGROUND

A wide variety of medical techniques and instruments have been developed for diagnosis and/or treatment within a patient's body, such as within a patient's gastrointestinal (GI) tract. Endoscopic mucosal resection (EMR), endoscopic sub-mucosal resection (ESR), polypectomy, mucosectomy, etc., are minimally invasive treatment methods for both malignant and non-malignant lesions. Endoscopic medical procedures, such as, for example, EMR, may be used to excise sessile adenomas or other unwanted tissue (e.g., tumors attached to a bodily surface) from the surface of an anatomical lumen. Such procedures often require the resection of one tissue plane while leaving an underlying tissue plane intact. Commonly, during such medical procedures, endoscopic medical devices (such as, for example, snares, graspers (e.g., hemostatic forceps), radiofrequency (RF) knifes, etc.) are inserted into the body, through the lumen of a delivery scope (such as, for example, an endoscope, gastroscope, colonoscope, bronchoscope, laryngoscope, cystoscope, duodenoscope, enteroscope, ureteroscope, etc., or another device having a lumen), and used for resecting tissue from a target site within the patient's body.

However, many conventional endoscopic medical devices operate in only one degree of freedom, for example, into and out of the delivery scope. In such devices, the distal tip of the delivery scope is deflected from side-to-side to move the medical device side-to-side within the body. That is, manipulation of the medical device inside the body is dependent on the tip deflection of the delivery scope used to insert the device into the body. Thus, the maneuverability of the endoscopic medical device and the ability to control the device within the body may be limited. Additionally, the user may be required to hold and/or manipulate the delivery scope with one hand, and hold and/or manipulate the medical devices introduced into the body through the delivery scope with the other hand. Additionally or alternatively, additional medical professionals may be required to assist the user with holding and/or manipulating the delivery scope and/or the inserted medical devices. These limitations may increase the duration, cost, and/or complexity of the medical procedure. Embodiments of the disclosed medical devices and methods may rectify some of the above-described deficiencies and/or address other aspects of the art. The scope of this disclosure, however, is defined by the attached claims, and not by the ability to solve any specific problem.

SUMMARY

Embodiments of this disclosure relate to, among other things, medical devices and methods for performing medical procedures using these medical devices. Each of the embodiments disclosed herein may include one or more of the features described in connection with any of the other disclosed embodiments.

In some embodiments, a medical device is disclosed. The medical device may include a handle, an end effector, and a tubular section extending between the handle and the end effector. The end effector may be configured to be rotated about a first axis extending through the tubular section without rotating the tubular section. And, the tubular section may be configured to be rotated about the first axis with the end effector.

Various embodiments of the disclosed medical device may alternatively or additionally include one or more of the following features: the handle may include a rotation actuator, wherein actuation of the rotation actuator may rotate the end effector about the first axis without rotating the tubular section; the end effector may be rotatably coupled to the tubular section such that the end effector can rotate about the first axis with the end effector; the handle may include an actuation actuator configured to actuate the end effector; the medical device may further include a core wire extending through the tubular section and coupled to the actuation actuator and the end effector, wherein actuation of the actuation actuator may cause translation of the core wire in the handle; the core wire may be rotatably coupled to the actuation actuator, and wherein actuation of the rotation actuator may rotate the core wire in the actuation actuator; wherein a cavity in the rotation actuator may accommodate the core wire and have one or a square, a rectangular, a triangular, or a polygonal cross-sectional shape; a hypotube may be attached to a portion of the core wire extending through the cavity of the rotation actuator, the hypotube may have a same cross-sectional shape as the cavity; actuation of the actuation actuator may cause the hypotube to translate with the core wire in the cavity of the rotation actuator; the medical device may further include (a) an articulation region coupled to a distal end of the tubular section and (b) a steering actuator on the handle, wherein actuation of the steering actuator may bend the articulation region in a first plane passing through the first axis; the medical device may further include one or more steering wires coupled to the steering actuator and extending through the articulation region along the first plane, wherein actuation of the steering actuator may apply tension to at least one of the one or more steering wires to bend the articulation region in the first plane; the articulation region may include multiple links that are rotatably coupled together; the one or more steering wires may include one steering wire or two steering wires.

In some embodiments, a method of using a medical device including a handle, an end effector, and a tubular section extending between the handle and the end effector is disclosed. The method may include rotating the end effector about a first axis extending through the tubular section, without rotating the tubular section. The method may also include rotating the tubular section about the first axis with the end effector.

Various embodiments of the disclosed method may alternatively or additionally include one or more of the following features: rotating the end effector may include actuating a rotation actuator on the handle, and rotating the tubular section may include rotating the handle; the method may further include inserting at least a portion of the tubular section into a body cavity prior to rotating the end effector and rotating the tubular section.

In some embodiments, a medical device is disclosed. The medical device may include a handle including a steering actuator, a rotation actuator, and an actuation actuator. The medical device may also include an end effector configured to be actuated by the actuation actuator, and a tubular section extending between the handle and the end effector. Actuation of the rotation actuator may be configured to rotate the end effector about a first axis extending through the tubular section without rotating the tubular section. And, rotation of the handle may be configured to rotate the tubular section about the first axis with the end effector.

Various embodiments of the disclosed medical device may alternatively or additionally include one or more of the following features: the medical device may further include a core wire coupled to the end effector and extending through the tubular section, the core wire may be coupled to the actuation actuator and the rotation actuator such that (a) actuation of the actuation actuator causes translation of the core wire in the handle, and (b) actuation of the rotation actuator rotates the core wire in the handle; the core wire may extend through a cavity in the rotation actuator, and wherein (a) the cavity may have one of a square, a rectangular, a triangular, or a polygonal cross-sectional shape, and (b) a hypotube may be attached to a portion of the core wire extending through the cavity, the hypotube may have the same cross-sectional shape as the cavity; actuation of the actuation actuator may cause the hypotube to translate with the core wire in the cavity.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of this disclosure and together with the description, serve to explain the principles of the disclosure. For simplicity and clarity of illustration, the figures depict the general structure and/or manner of construction of the various embodiments described herein. Descriptions and details of well-known features and techniques may be omitted for brevity and to avoid obscuring other features. Elements in the figures are not necessarily drawn to scale. The dimensions of some features in the illustrated figures may be exaggerated relative to other features to improve understanding of the exemplary embodiments. Cross-sectional views are simplifications provided to help illustrate the relative positioning of various regions and/or components. One skilled in the art would appreciate that the cross-sectional views are not drawn to scale and should not be viewed as representing proportional relationships between different regions and/or components.

FIGS. 3A-3C illustrate different views of an exemplary handle of the medical device of FIG. 2.

FIGS. 4A-4F illustrate different regions/components of the handle of the medical device of FIG. 2.

FIGS. 6A-6G illustrate different regions/components of the articulation region of the medical device of FIG. 2.

DETAILED DESCRIPTION

It should be noted that the description set forth herein is merely illustrative in nature and is not intended to limit the embodiments of the subject matter, or the application and uses of such embodiments. Any device, method, or implementation described herein as exemplary is not to be construed as preferred or advantageous over other implementations. Rather, the term "exemplary" is used in the sense of example or "illustrative," rather than "ideal." The terms "comprise," "include," "have," "with," and any variations thereof are used synonymously to denote or describe a non-exclusive inclusion. As such, a device or a method that uses such terms does not include only those elements or steps, but may include other elements and steps not expressly listed or inherent to such device and method.

The terms "proximal" and "distal" are used herein to refer to the relative positions of the components of the medical system or medical device being described. As used herein, "proximal" refers to a position relatively closer to the exterior of the body or closer to a medical professional using the system or device. In contrast, "distal" refers to a position relatively further away from the medical professional using the system or device, or closer to the interior of the body. Further, as used herein, the terms "first," "second," and the like, do not denote any order, quantity, or importance, but rather are used to distinguish one element from another. Similarly, terms of relative orientation, such as "top," "bottom," "left," "right," etc. are used with reference to the orientation of the structure illustrated in the figures being described. Moreover, the terms "a" and "an" herein do not denote a limitation of quantity, but rather denote the presence of at least one of the referenced item. Further, all relative terms such as "about," "substantially," "approximately," etc. are used to indicate a possible variation of ±10% (unless noted otherwise or another variation is specified). Moreover, in the claims, values, limits, range of values (e.g., range of thickness, etc.) mean the value, limit, and/or range ±10%.

Examples of this disclosure include medical devices and methods for using these medical devices in a medical procedure. Reference will now be made in detail to the examples described above and illustrated in the accompanying drawings. Wherever possible, the same reference numbers will be used to refer to the same or like parts.

Figure 1:
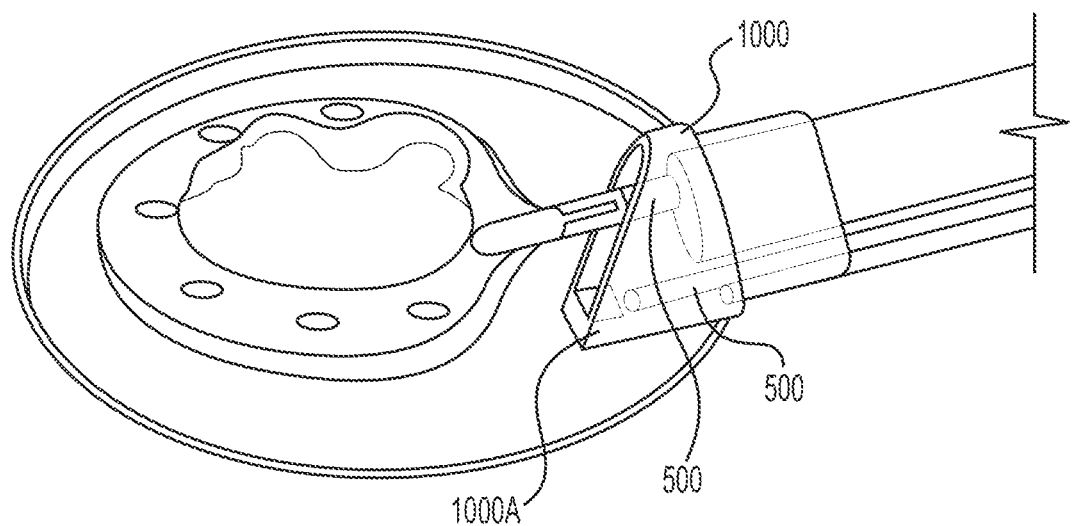
FIG. 1 illustrates medical devices of this disclosure performing an exemplary medical procedure.
Figure 2:
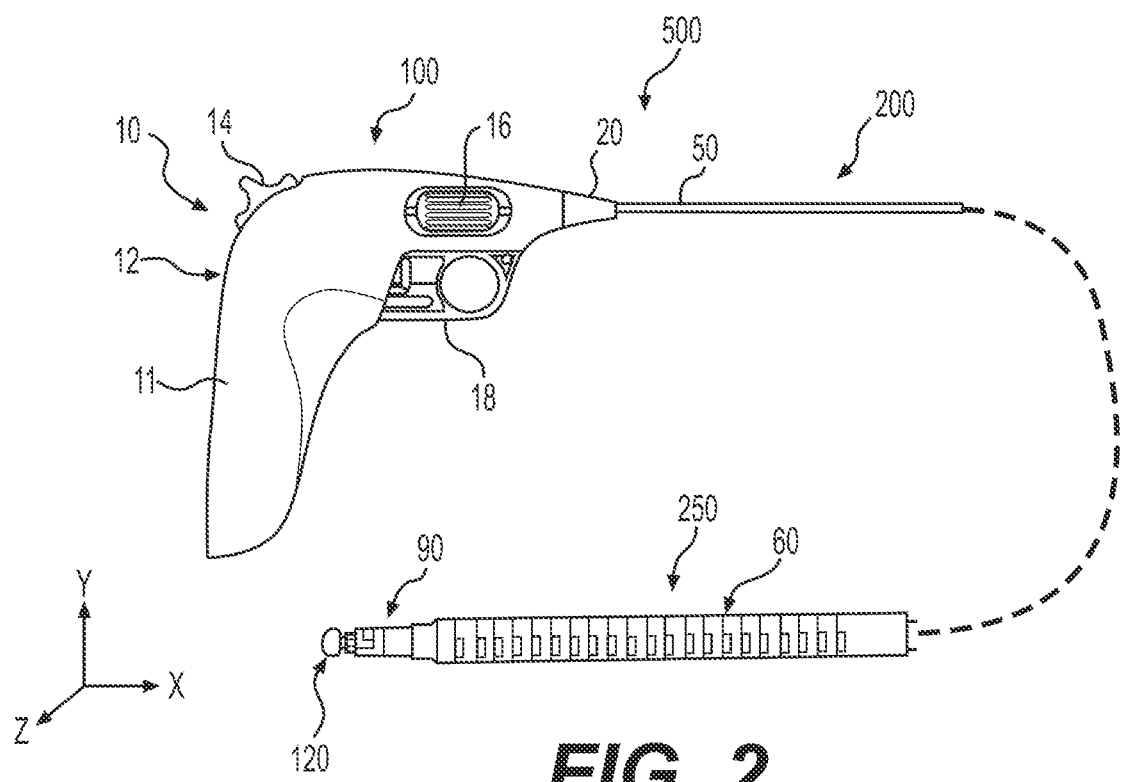
FIG. 2 illustrates an exemplary medical device used in the medical procedure of FIG. 1.

FIG. 1 illustrates an exemplary medical procedure being performed at a target location within a patient's body using exemplary medical devices 500 of this disclosure. FIG. 2 illustrates an exemplary medical device 500 used in the medical procedure of FIG. 1. In the discussion below, reference will be made to both FIGS. 1 and 2. In some embodiments, as illustrated in FIG. 1, medical devices 500 may be introduced into the body through the lumen of a delivery scope 1000. Any suitable delivery scope 1000 (such as, for example, gastroscopes, colonoscopes, bronchoscopes, laryngoscopes, cystoscopes, duodenoscopes, enteroscopes, ureteroscopes, catheters, etc.) may be used to introduce medical devices 500 into the body. In some embodiments, medical device 500 may be configured to be inserted into the body through a delivery scope having, for example, a 2.8 mm diameter lumen. As previously explained, the use of a delivery scope 1000 to insert medical devices 500 into the body is not a requirement. For example, it is contemplated that, in some embodiments, medical devices 500 may be inserted into the body directly (e.g., without using a delivery scope). The disclosed medical devices 500 may be used to perform any suitable medical procedure at any suitable location of the patient's anatomy (such as, for example, portions of the large intestine, small intestine, cecum, esophagus, other portions of the gastrointestinal tract, cardiovascular, reproductive, etc.). For example, one or more medical devices 500 may be used to visualize, cut, resect, energize, treat, remove, couple, and/or manipulate target tissue in an endo-luminal space, or facilitate the process thereof.

During a medical procedure, the delivery scope 1000 may be inserted into the body of the patient through a natural orifice (mouth, rectum, etc.), or an incision, and pushed in such that its distal end 1000A is positioned at a desired worksite (e.g., a tissue lesion, etc.) within the body. An end effector 120, at the distal-most end of medical device 500, is then inserted into a lumen of delivery scope 1000 through its proximal end, and pushed in such that the end effector 120 extends out of the distal end 1000A of delivery scope 1000 into the body. For example, with reference to the XYZ triad illustrated in FIGS. 1 and 2, when medical device 500 is pushed into delivery scope 1000 from the proximal end, the end effector 120 of medical device 500 moves in the −X direction out of the distal end 1000A of delivery scope 1000. That is, translation of end effector 120 of medical device 500 along the X-axis at the worksite is achieved by pushing and pulling medical device 500 into and out of delivery scope 1000. Conventionally, translation of the end effector 120 in the YZ plane (i.e., movement in the Y direction or the Z direction, referred to herein as side-to-side motion) is achieved by moving the distal end 1000A of the delivery scope 1000 side-to-side. That is, manipulation of conventional medical devices inserted into the body via a delivery scope is achieved largely via manipulation of the delivery scope. In contrast, in some embodiments of this disclosure, the disclosed medical devices 500 may be manipulated at the target site (e.g., moved towards and away from tissue, moved side-to-side, rotated, actuated, etc.) independent of the delivery scope 1000. Therefore, aspects of the disclosed medical devices 500 may provide the user with the ability to separately control some or all of the position, direction, movement, and actuation of medical devices 500 independent of the delivery scope 1000.

In general, the disclosed medical devices 500 may include any type of end effector 120 suitable for the medical procedure being performed. For example, the disclosed medical devices 500 may include an end effector 120 in the form of one or more of a clip, a snare, a grasper, a camera, an illumination device, a needle, a knife, scissors, forceps, an electrosurgical knife (e.g., an endoscopic submucosal dissection knife), etc. For the sake of simplicity, however, in the discussion below, an end effector 120 having the configuration of a grasper will be used to describe aspects of this disclosure. However, it should be noted that the concepts described with reference to the grasper may be applied to an endoscopic medical device 500 having any type of end effector 120. Components of medical device 500 may be made of, or include, any suitable biocompatible material (such as, for example, a metallic material, a plastic material, a shape memory metal (such as Nitinol), a shape memory polymer, a polymer, or any combination of biocompatible materials).

With reference to FIG. 2, medical device 500 may include a proximal manipulation portion 100 and a distal insertion portion 200. Manipulation portion 100 includes a handle 10 having controls that may be used to manipulate medical device 500, for example, within the patient's body. Handle 10 is configured to be held by a user (medical professional, etc.) during use of device 500, and may be configured in accordance with human factor interface design (HFID) principles. Insertion portion 200 includes a flexible tubular section 50 (or a core) that extends from handle 10 to a distal portion 250 of the device 500. It should be noted that the distal portion 250 is shown exaggerated in FIG. 2 to clearly illustrate structural features of this portion. The flexible nature of the tubular section 50 enables it to bend and flex while device 500 is introduced into the body through the lumen of delivery scope 1000. Distal portion 250 of the device 500 includes, among other regions, an articulation region 60, a rotation region 90, and the end effector 120. These regions of distal portion 250 will be described in detail later.

Handle 10 includes a body 12 coupled to tubular section 50 at a sleeve cap 20. Body 12 includes a gripping portion 11 that may be generally shaped to be held by the hand (left or right hand) of the user. Body 12 also supports control devices, actuation devices, or actuators, which may be used to manipulate the distal portion 250 and the end effector 120 of the device 500. In the discussion below, these actuation device will be referred to as "knobs." It should be noted, however, that reference to actuation devices as knobs is merely for the sake of convenience and is not as an indication of their geometry. In some embodiments, the actuation devices on handle 10 may include a first actuator (referred to herein as a steering knob 14), a second actuator (referred to herein as a rotation knob 16), and a third actuator (referred to herein as an actuation knob 18).

With reference to FIG. 2, during use of device 500, the steering knob 14 may be used to steer, or move, the end effector 120 and the distal end of device 500 from side-to-side (e.g., in any direction in the YZ plane). Rotation knob 16 may be used to rotate the end effector 120 independent of distal portion 250, for example, about the X-axis. And, actuation knob 18 may be used to actuate, for example, open and close, the end effector 120. The end effector 120 (along with the distal end of device 500) may be moved in the X direction by moving the handle 10 in the X direction (e.g., by pushing device 500 into and out of delivery scope 1000). And as will be described in more detail later, the tubular section 50 may be rotated, for example, about the X-axis, by rotating the handle 10 which will rotate the distal portion 250 and end effector 120 together.

It should be noted that, although a specific configuration of the handle 10 is illustrated in FIG. 2, this is only exemplary. In general, handle 10 may have any configuration and its control knobs may have any suitable configuration, and may be positioned at any location. In some embodiments, the shape of the handle 10 and the location of the steering knob 14, the rotation knob 16, and the actuation knob 18 on the handle 10 may be determined based on HFID principles. In some embodiments, when the gripping portion 11 of the handle 10 is grasped by a user's hand, the thumb may be used to activate the steering knob 14, the middle finger may be used to activate the actuation knob 18, and the forefinger may be used to activate the rotation knob 16. Among other possible modifications, in some embodiments, the locations of rotation knob 16 and actuation knob 18 on handle 10 may be interchanged. It should be noted that, the disclosed actuating system (e.g., steering knob 14, the rotation knob 16, and the actuation knob 18) on handle 10 has many advantages when compared with actuation systems of known medical devices and endoscopes. One advantage is that some or all of the disclosed actuators (e.g., steering knob 14, the rotation knob 16, and/or the actuation knob 18) enable a long stroke of the steering wires 32, 34 and/or the pull wire 36, which translates to more motion at the distal end of device 500. Another advantage is that the disclosed actuators of handle 10 provide mechanical advantage as compared to actuation systems of known devices and endoscopes that have limited mechanical advantage. Increasing mechanical advantage of an actuator reduces the force and effort needed to actuate the actuator.

Figure 3A:
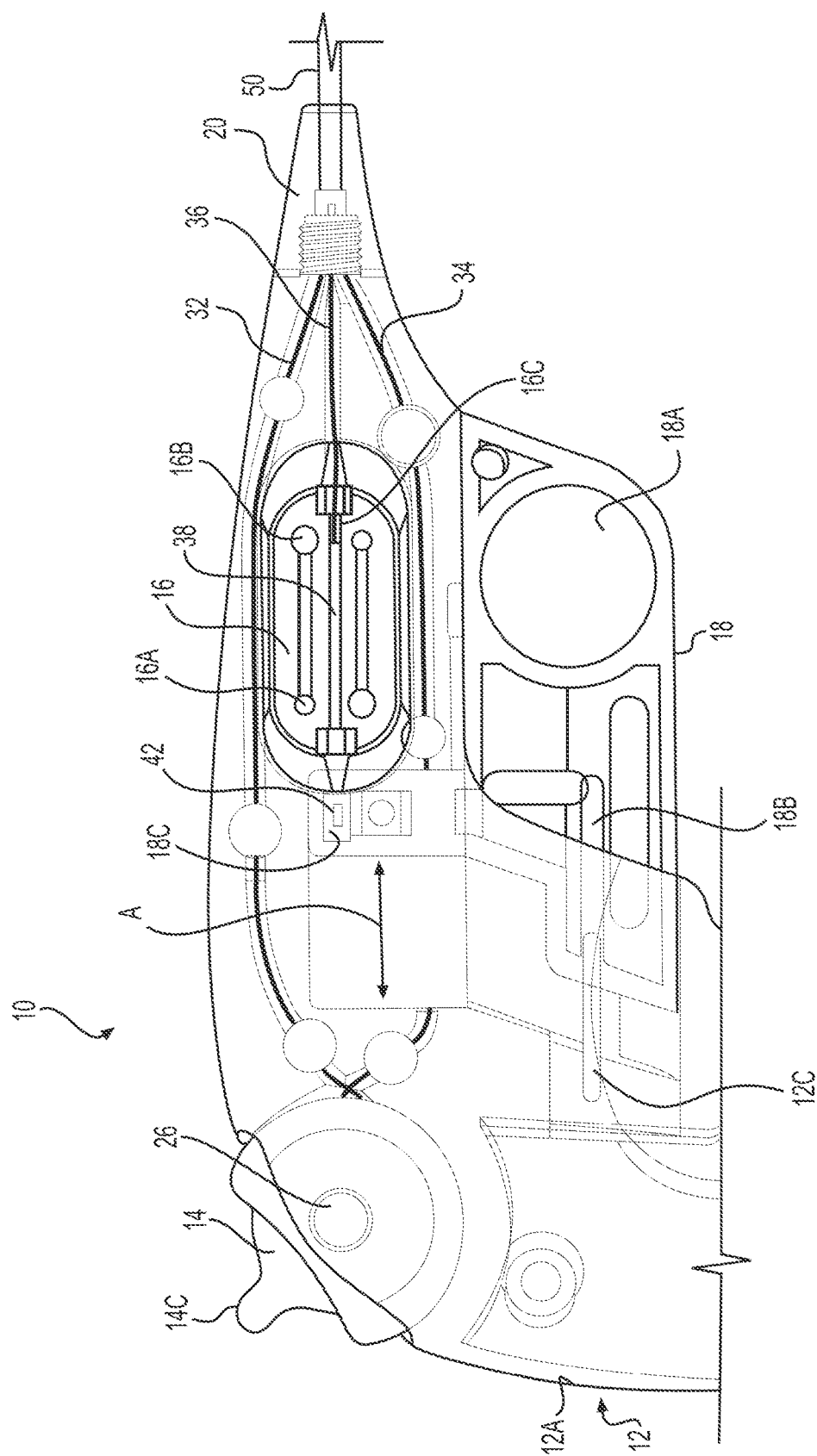

FIGS. 3A-3C are illustrations of different views of an exemplary handle 10 of device 500. Body 12 of handle 10 may include two parts or two halves—a first part 12A and a second part 12B—which when joined together form the two opposite sides of the handle 10. FIG. 3A is a side view of handle 10 with its second part 12B shown in shadow to illustrate the components and features within the handle 10. And, FIGS. 3B and 3C are side views of the first and second parts 12A, 12B, respectively, of handle 10. In the discussion below, reference will be made to FIGS. 3A-3C. When first part 12A is joined with second part 12B to assemble handle 10, pins 24A on first part 12A engage with (e.g., forms an interference fit with) corresponding pin slots 24B in second part 12B to couple the two parts together. The two parts 12A and 12B can be joined by other means like press fit, glue together. First and second parts 12A and 12B include recesses or cavities configured to support the steering knob 14, the rotation knob 16, and the actuation knob 18. When the handle 10 is assembled: the steering knob 14 is supported between cavities 14A and 14B of the first and second parts 12A, 12B; the rotation knob 16 is supported in cavities 16A and 16B of the first and second parts 12A, 12B; and the actuation knob 18A is supported between cavities 18A and 18B of the first and second parts 12A, 12B. First and second parts 12A, 12B also include external (e.g., male) screw threads 20A, 20B that are configured to engage with corresponding screw threads on the sleeve cap 20 to couple the sleeve cap 20 to the handle 10.

With reference to FIG. 3A, steering wires 32, 34 extend through recessed pathways on body 12 of handle 10 from an end proximate the sleeve cap 20 to the steering knob 14. One end of each of the steering wires 32, 34 is coupled to steering knob 14, and the opposite end of each of the steering wires 32, 34 is coupled to an articulation cap 68 (see FIG. 7A) in the distal portion 250 of device 500 (see FIG. 2). In general, the steering wires 32, 34 may be coupled to the steering knob 14 and the articulation cap 68 in any suitable manner, such as, for example, by crimping, welding, using a fastener, mechanical locking feature, tie knot, etc. With reference to FIGS. 3B and 3C, first part 12A includes steering wire slots 32A, 34A, and second part 12B includes steering wire slots 32B, 34B, that are together configured to receive the steering wires 32, 34 when handle 10 is assembled. In some embodiments, first part 12A may include pins 22A located on steering wire slots 32A, 34A, and second part 12B may include correspondingly located recesses 22B configured to receive these pins 22A when handle 10 is assembled. Pins 22A may include a transverse pathway or slot 22C (see FIG. 4B) at its base extending over steering wire slot 32A, 34A to permit the steering wires 32, 34 to pass therethrough.

Figure 11A:
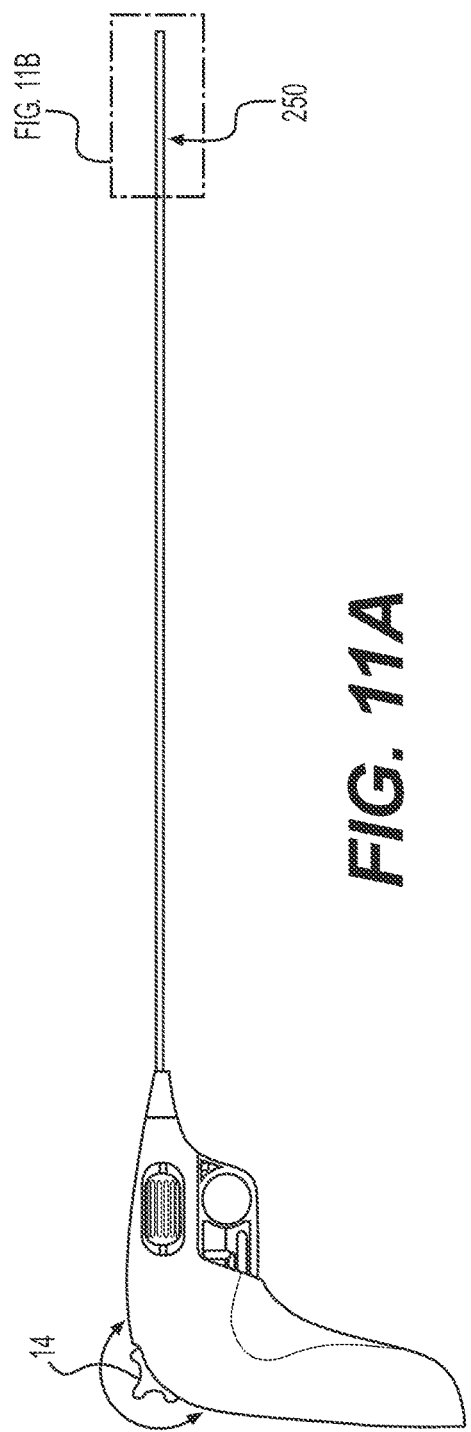
FIGS. 11A-11G are schematic illustrations of exemplary operating modes of the medical device of FIG. 2
Figure 11B:
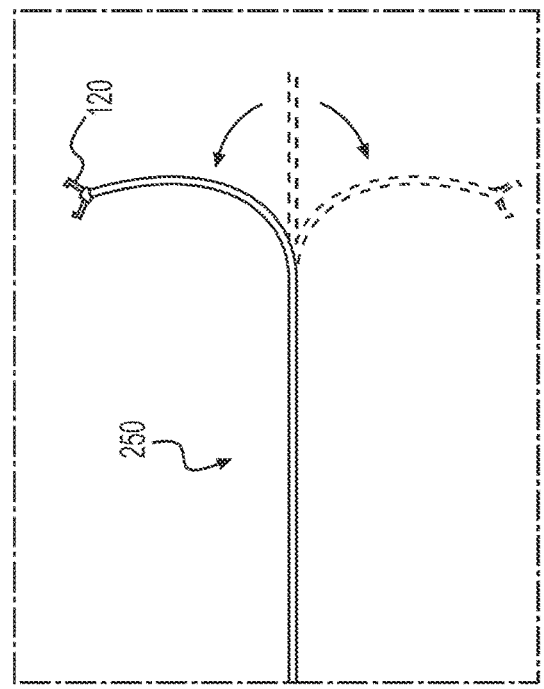

FIG. 4A is an enlarged view of the portion of body 12 that supports steering knob 14, and FIG. 4B is an enlarged view of the corresponding portion of first part 12A of body 12. As best seen in FIG. 4A, pivots 26 project outwards from opposite side surfaces of the steering knob 14. When the handle 10 is assembled with steering knob 14 positioned in the steering knob cavities 14A, 14B of the first and second parts 12A, 12B, pivots 26 will be received in recesses 26A, 26B (see FIGS. 3B, 3C) on the first and second parts 12A, 12B (see FIG. 4A). After assembly of the handle 10, an extension 14C of steering knob 14 protrudes from the body 12 of handle 10. To actuate the steering knob 14, the user may apply a force (push or pull) on the extension 14C to rotate the steering knob 14 (as illustrated by the double-headed arrow on FIG. 4A) about its pivots 26. When the steering knob 14 is actuated, or rotated about its pivots 26, the resulting forces (e.g., tension) on the steering wires 32, 34 cause links in the articulation region 60 of device 500 to rotate about their respective pivots, and cause the distal end of the device 500 to move side-to-side. For example, as schematically illustrated in FIGS. 11A and 11B, when the steering knob 14 is rotated in one direction (e.g., clockwise), a pulling force (or tension) is applied to one of the steering wires (e.g., steering wire 32). And, when the steering knob 14 is rotated in the opposite direction (e.g., counter-clockwise), a pulling force is applied to the other steering wire (e.g., steering wire 34). The direction of articulation is controlled by the location of steering wire 32 or 34 crimping on the steering knob 14. When the steering wire 32 is crimped into the hole 14 E and steering wire 34 is crimped into hole 14D, the steering knob 14 rotation in clock wire direction puts the steering wire 32 in tension. In other concept, if the crimping location is interchanged, steering wire 32 crimped in hole 14D and steering wire 34 in 14E, steering knob 14 clockwise rotation will put steering wire 34 in tension. As will be described in more detail later, when tension is applied to steering wire 32, the articulation region 60 bends (or curves) in the direction of steering wire 32, and when tension is applied to steering wire 34, the articulation region 60 bends in the direction of steering wire 34. The bending of the articulation region 60, resulting from the actuation of the steering knob 14, causes the end effector 120 at the distal end of device 500 to move side-to-side.

Figure 4C:
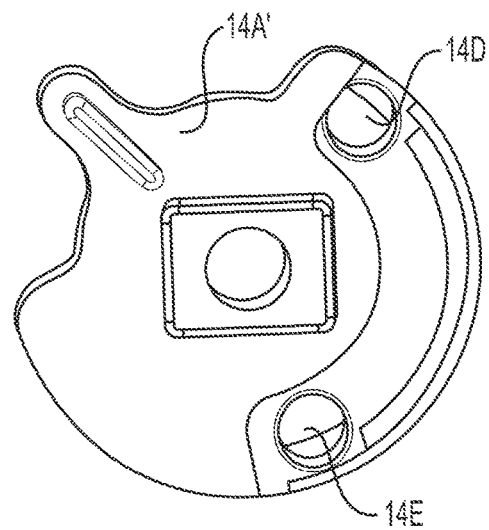
Figure 4D:
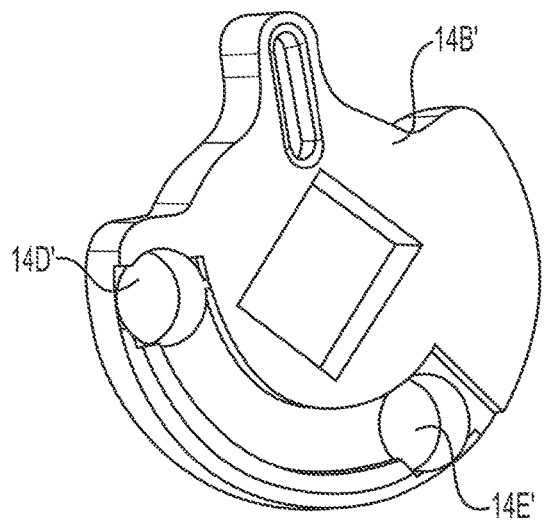

In some embodiments, similar to body 12, the steering knob 14 may also include a first part 14A' and a second part 14B' that may be joined together to form the steering knob 14. FIGS. 4C and 4D illustrate the first and second parts 14A', 14B' of steering knob 14 in an exemplary embodiment. As illustrated in FIG. 4C, first part 14A' of the steering knob 14 may include holes or cavities 14D and 14E configured to receive locking features (not shown) of the steering wires 32, 34 and couple the steering wires 32, 34 to the steering knob 14. Second part 14B' of the steering knob 14 may include recessed regions 14D' and 14E' configured to receive the locking features of the steering wires 32, 34 that are received in cavities 14D and 14E of first part 14A'. In some embodiments, these locking features may include a crimp, lock nut, or another feature attached to an end of each of the steering wires 32, 34. The locking feature of each steering wire 32, 34 may engage with a different one of cavities 14D and 14E to couple both steering wires 32, 34 to steering knob 14.

It should be noted that the geometry, configuration, and features of steering knob 14 described above are only exemplary. In general, steering knob 14 may have a different configuration, for example, as described with reference to FIGS. 10A-10D. In some embodiments, the steering knob 14 may be configured as a joy stick or a cylindrical component with surface features to increase grip. As a person of ordinary skill in the art would recognize, any type of actuation device that is adapted to selectively apply tension to the steering wires 32, 34 may be used as the steering knob of handle 10. In general, any type of wire (single strand, multi-strand, etc.), made of any material (e.g., stainless steel, Nitinol, nylon, etc.) having any dimension may be used as steering wires 32, 34. In some embodiments, the steering wires 32, 34 may be coated with or include a sleeve made of a different material (e.g., a lubricious material). Since steering wires 32, 34 that may be used with endoscopic medical devices are known in the art, they are not described in detail herein.

Referring back to FIG. 3A, in addition to steering wires 32 and 34, a core wire or a pull wire 36 (or a control element) also extends through the body 12 of handle 10. The passageways on handle 10 through which the pull wire 36 and the steering wires 32, 34 extend may be sized such that these wires pass freely through their respective passageways without interference. In some embodiments, a tube made of a lubricious material, such as, for example, polytetrafluoroethylene (PTFE) may be provided in, or attached in, some or all of these passageways to promote free movement of the wires therein. Like the steering wires 32, 34, the pull wire 36 may also include any type of wire (single strand, multi-strand, etc.), made of any material (e.g., stainless steel, Nitinol, nylon, etc.) having any dimension. In some embodiments, the pull wire 36 may be coated with or include a sleeve made of a different material (e.g., a lubricious material).

The pull wire 36 may be coupled to the rotation knob 16 and the actuation knob 18. At its proximal end, the pull wire 36 is fixedly coupled (or attached) to a sleeve 42 that is rotatably coupled to the actuation knob 18. That is, sleeve 42 is coupled to the actuation knob 18 such that it can rotate with the square sleeve 38 in the rotation knob 16 and translate with the actuation knob 18. The pull wire 36 may be attached to the sleeve 42 in any manner (welded, crimped, glued, etc.). In some embodiments, the pull wire 36 may be crimped to the sleeve 42. Sleeve 42 may be rotatably positioned in the actuation knob 18 in any manner. The pull wire 36 extends distally from the handle 10 to the distal portion 250 of the device 500 (see FIG. 2) through sleeve cap 20. At its distal end, pull wire 36 is coupled to the end effector 120 such that, when the actuation knob 18 is moved forwards (i.e., moved distally) and backwards (i.e., moved proximally), the end effector 120 operates (e.g., opens and closes in an embodiment where the end effector 120 is a grasper).

The pull wire 36 also extends through a channel 16C in the rotation knob 16. In some embodiments, channel 16C may have a square cross-sectional shape. A correspondingly shaped hypotube (e.g., a square hypotube 38) may be slidably positioned in channel 16C. That is, the square hypotube 38 is configured to slide back and forth in channel 16C of the rotation knob 16. The square hypotube 38 may be fixedly coupled (e.g., crimped) to the pull wire 36 that extends therethrough. Due to the square cross-sectional shape of channel 16C and hypotube 38, when the rotation knob 16 is rotated, the hypotube 38 and the pull wire 36 rotate with the rotation knob 16, thereby rotating the end effector 120 independent of distal shaft 250. Since the hypotube 38 is slidably coupled to the rotation knob 16, when the actuation knob 18 is moved back and forth, the hypotube 38 and pull wire 36 translate in the rotation knob 16 with the actuation knob 18. Since the sleeve 42 is rotatably coupled to the actuation knob 18, when the rotation knob 16 rotates, the pull wire 36 and the sleeve 42 rotate in the actuation knob 18.

It should be noted that the specific configuration of the hypotube 38 and the channel 16C described above is only exemplary and many variations are possible. For example, although the cross-sectional shape of channel 16C and hypotube 38 is described as being square, this is only exemplary. In general, the channel 16C and the hypotube 38 may have any suitable non-circular shape (triangular, polygonal, hexagonal, rectangular, etc.). It should also be noted that the coupling of the pull wire 36 to rotation knob 16 described above is only exemplary. In general, the pull wire 36 may be coupled to the rotation knob 16 in any manner such that the pull wire 36 rotates with the rotation knob 16 and translates with the actuation knob 18.

Similar to steering knob 14, the rotation knob 16 may also have two parts, or halves, that join together to form the complete rotation knob 16 when the handle 10 is assembled. Note that FIG. 3A illustrates one half of the rotation knob 16 and FIG. 2 illustrates the complete rotation knob 16. The two halves of the rotation knob 16 may have mating features that engage with each other to couple the two halves together when the handle 10 is assembled. These mating features may also assist in aligning the two parts 12A and 12B of the body 12 together when the handle 10 is assembled. In some embodiments, as illustrated in FIG. 3A, these mating features may include pins 16A and correspondingly shaped cavities 16B (in both halves of the rotation knob 16) that engage with each other to couple the two halves of the rotation knob 16 together when the handle 10 is assembled. With reference to FIG. 2, the external surface of the rotation knob 16 may have features (e.g., grooves, etc.) that provide grip to the user during use. It should be noted that although the rotation knob 16 is illustrated as having a cylindrical configuration with grooves on the surface (or a thumbwheel), this is only exemplary. As a person of ordinary skill in the art would recognize, the rotation knob 16 may have any suitable configuration.

The actuation knob 18 enables the user to operate or actuate the end effector 120 of device 500. For example, in embodiments where the end effector 120 is a grasper with jaws that open and close when actuated, the actuation knob 18 may be used to open and close the jaws. For example, moving the actuation knob 18 proximally may close the jaws, and moving the actuation knob 18 in the opposite distal direction may open the jaws (or vice versa). Actuation knob 18 includes a cavity or a slot 18A that serves as an interface (e.g., a finger interface) for the user. In use, the user may insert a finger though slot 18A and pull and push the actuation knob 18 proximally and distally to actuate the end effector 120. The stroke (i.e., the length labeled A in FIG. 3A) of the actuation knob 18 may enable the jaws to open and close by different amounts. For example, moving the actuation knob 18 by a distance of, for example, ⅓ A may open and close the jaws of the end effector 120 by a smaller amount than moving the jaws by a distance of A. Body 12 (e.g., first part 12A and second part 12B of body 12) of the handle 10 and the actuation knob 18 have correspondingly located mating features that engage with each other to enable the actuation knob 18 to move in a predefined path (e.g., linear path, etc.) in the handle 10. These mating features may include a linear cavity 18B on the actuation knob 18, and mating projections 12C on the first and second parts 12A, 12B of body 12 that fits into cavity 18B. For example, when the handle 10 is assembled, the projections 12C of the first and second part 12A, 12B join to form a single projection that fits into the elongate cavity 18B in the actuation knob 18 (see FIGS. 3B, 3C) to enable the actuation knob 18 to slide along the path defined by the cavity 18B. Actuation knob 18 may also include additional features (e.g., projections, cavities, etc.) (not labeled in the figures) that mate with corresponding features on the handle body 12 to align the actuation knob 18 on handle 10.

As explained previously, the actuation knob 18 includes a sleeve 42 that the pull wire 36 is attached to. The sleeve 42 is rotatably secured in a cavity 18C formed in the actuation knob 18. Sleeve 42 is positioned in cavity 18C in a manner such that (a) the sleeve 42 and the pull wire 36 can together rotate in actuation knob 18 when rotation knob 16 is rotated, and (b) the sleeve 42 and the pull wire 36 move along with the actuation knob 18 when the actuation knob 18 is translated (proximally and distally). It should be noted that the configuration of the actuation knob 18 illustrated in FIG. 3A is only exemplary and medical device 500 can include an actuation knob 18 having any suitable configuration.

Figure 4E:
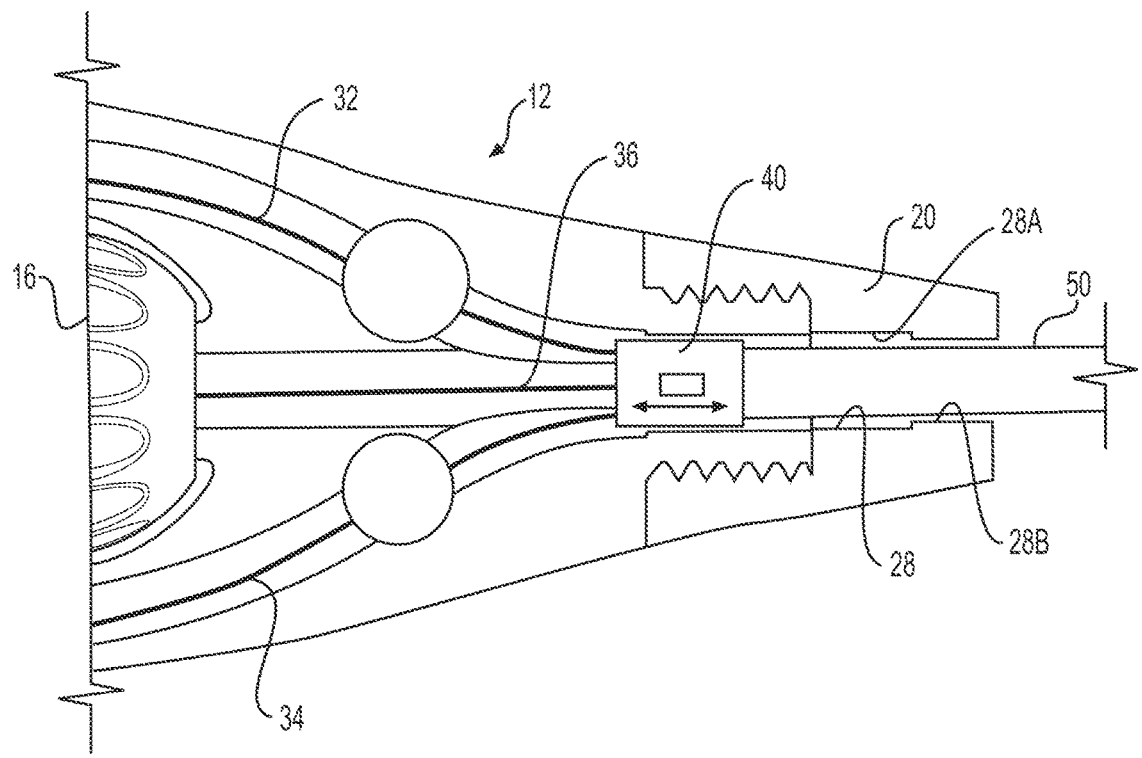
Figure 4F:
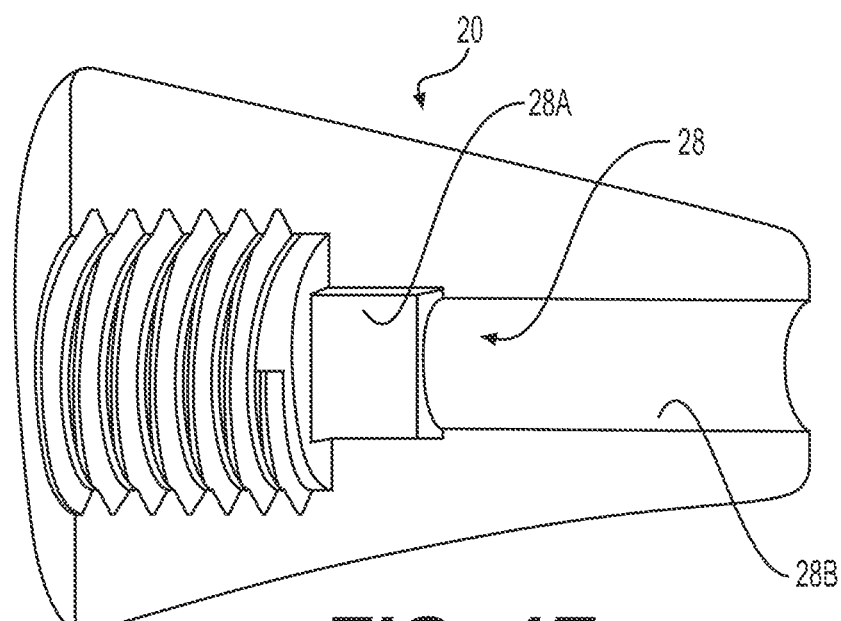

As explained previously, the pull wire 36 and the steering wires 32, 34 of handle 10 extend to the distal portion 250 of the device 500 through the tubular section 50. Handle 10 is coupled to the tubular section 50 using sleeve cap 20. FIG. 4E is an illustration of an exemplary sleeve cap 20 coupling handle 10 with tubular section 50. And, FIG. 4F is a sectional view of a sleeve cap 20 in an exemplary embodiment. As illustrated in FIG. 4E, in some embodiments, a threaded screw (e.g., a female threaded screw) of the sleeve cap 20 may engage with a corresponding threaded screw (e.g., a male threaded screw) of the handle body 12 to couple handle 10 to the tubular section 50. It should be noted that, although the sleeve cap 20 is described as being attached to the handle 10 using threaded screws, this is only exemplary. In general, the sleeve cap 20 may be attached to the handle 10 in any manner (male threaded screw on sleeve cap 20 engaging with female threaded screw of handle 10, glued, using pins, etc.). When the sleeve cap 20 is coupled to the handle 10, a central passageway 28 of the sleeve cap 20 may fluidly couple with the passageways of handle 10 through which the pull wire 36 and steering wires 32, 34 extend. Passageway 28 has a stepped configuration with a first portion 28A proximate handle 10 having a larger width/diameter and a second portion 28B proximate tubular section 50 having a smaller width/diameter. In the embodiment of sleeve cap 20 illustrated in FIG. 4F, the first portion 28A of passageway 28 has a square (or rectangular) configuration having a larger width, and the second portion 28B has a tubular configuration with a smaller width (or diameter).

The proximal end of the tubular section 50 is coupled to a wire sleeve 40, and the distal end of the tubular section 50 is coupled to the articulating section 60 in the distal portion 250 of device 500. In some embodiments, the wire sleeve 40 may be fixedly attached to (e.g., crimped to) the proximal-most end of the tubular section 50. Wire sleeve 40 may be positioned in first portion 28A of sleeve cap 20 (see FIG. 4E). The wire sleeve 40 may have a shape or configuration similar to the shape or configuration of the first portion 28A of passageway 28 (where the wire sleeve 40 is positioned in). That is, in embodiments where first portion 28A has a square or rectangular shape, the wire sleeve 40 also has a corresponding square or rectangular shape. The outer width of the wire sleeve 40 may be smaller than the width of the first portion 28A (of passageway 28) and larger than the width of the second portion 28B such that, when sleeve cap 20 is attached to handle 10, the smaller width of the second portion 28B prevents the wire sleeve 40 (and the tubular section 50) from being separated from sleeve cap 20. Since the width of the first portion 28A is larger than the width of the wire sleeve 40, a gap or a clearance exists between the wire sleeve 40 and the sleeve cap 20 in passageway 28. As illustrated using the double-headed arrow in FIG. 4E, when the sleeve cap 20 is coupled to handle 10, the passageways in the handle 10 and the first portion 28A of passageway 28 collectively form a combined passageway having a larger width than the wire sleeve 40. This combined passageway enables the wire sleeve 40 and the tubular section 50 to freely translate (e.g., linearly) within the sleeve cap 20 and the distal end of the handle 10, for example, when device 500 is inserted into the lumen of delivery scope 1000. The ability of the wire sleeve 40 and the tubular section 50 to freely translate in this manner enables the tubular section 50 to extend through a tortuous lumen of the delivery scope 1000 without inducing tension therein.

The steering wires 32, 34 and the pull wire 36 extend from handle 10 to the tubular section 50 through the tubular section 50. Wires 32, 34, 36 extend through the tubular section 50 such that they can move (rotate, translate, etc.) relative to, and independent of each other. For example, when steering knob 14 is turned to apply tension to steering wires 32, 34, these steering wires 32, 34 can translate in tubular section 50 (i.e., translate relative to the tubular section 50). Similarly, when rotation knob 16 is rotated to rotate the pull wire 36, and when actuation knob 18 is translated to translate the pull wire 36, the pull wire 36 can rotate and translate in the tubular section without moving the tubular section 50.

As explained above, in some embodiments, as illustrated in FIG. 4F, the first portion 28A of passageway 28 (of sleeve cap 20) has a square or rectangular configuration. In some such embodiments, the wire sleeve 40 that is positioned in the first portion 28A may also have a corresponding square (or rectangular) configuration, such that, when the handle 10 is rotated, the wire sleeve 40 and the tubular section 50 coupled to wire sleeve 40 also rotate along with the handle 10. It should be noted that, in general, the first portion 28A of passageway 28 and the wire sleeve 40 may have any configuration (e.g., triangular, polygon, etc.) that enables the rotation of the handle 10 to rotate the tubular section 50.

Figure 11C:
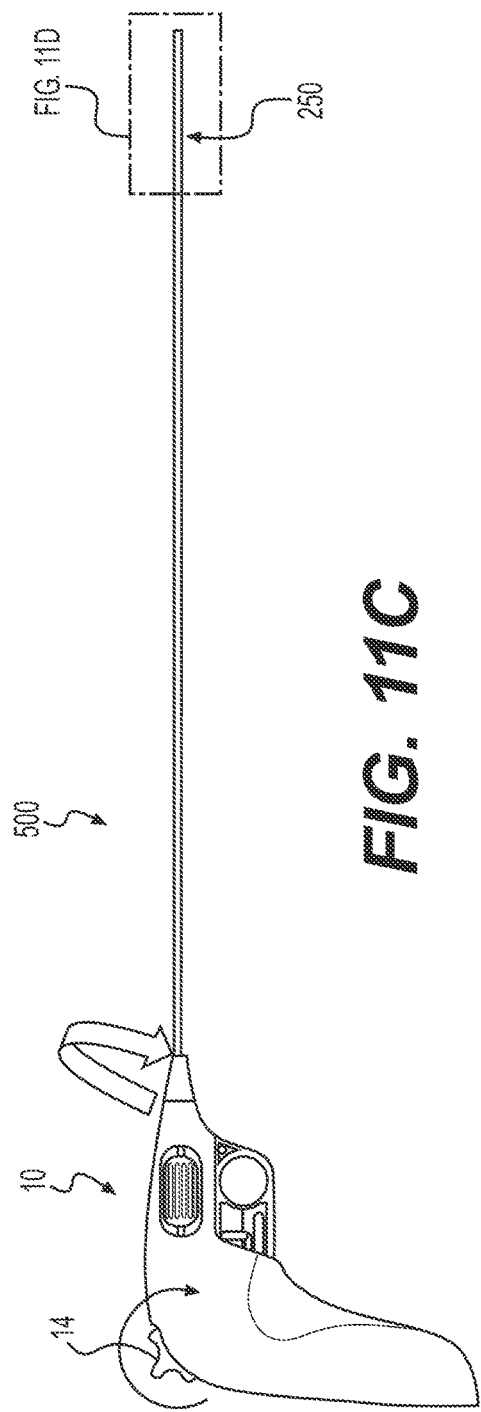
Figure 11D:
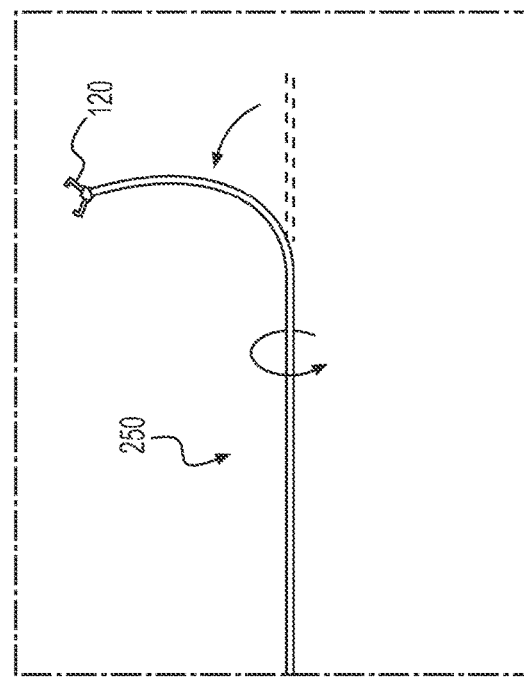

As explained above, the distal end of the pull wire 36 is coupled to the end effector 120, and the distal end of the tubular section 50 is coupled to the articulating section 60 (see FIG. 2). Since the pull wire 36 that extends through the tubular section 50 is not coupled to the wire sleeve 40, when the handle 10 is rotated, the wire sleeve 40, the tubular section 50, distal portion 250 and distal assembly 120 rotates together. As schematically illustrated in FIGS. 11B and 11C, the user can rotate the steering knob 14 (e.g., in clockwise direction) to articulate in side direction, and the handle 10 can be rotated along with articulation distal portion 250 to reach the target tissue. This is. Similarly, when rotation knob 16 is rotated to rotate the pull wire 36, the pull wire 36 rotates in tubular section 50 without rotating the tubular section 50 Therefore, rotation of the rotation knob 16 rotates the pull wire 36 and the end effector 120 independent of the tubular section 50, and rotation of the handle 10 rotates the articulation region 60 along with end effector 120. As will be explained later, rotating the articulation region 60 enables the end effector 120 to be moved side-to-side in different directions in the YZ plane.

Figure 5A:
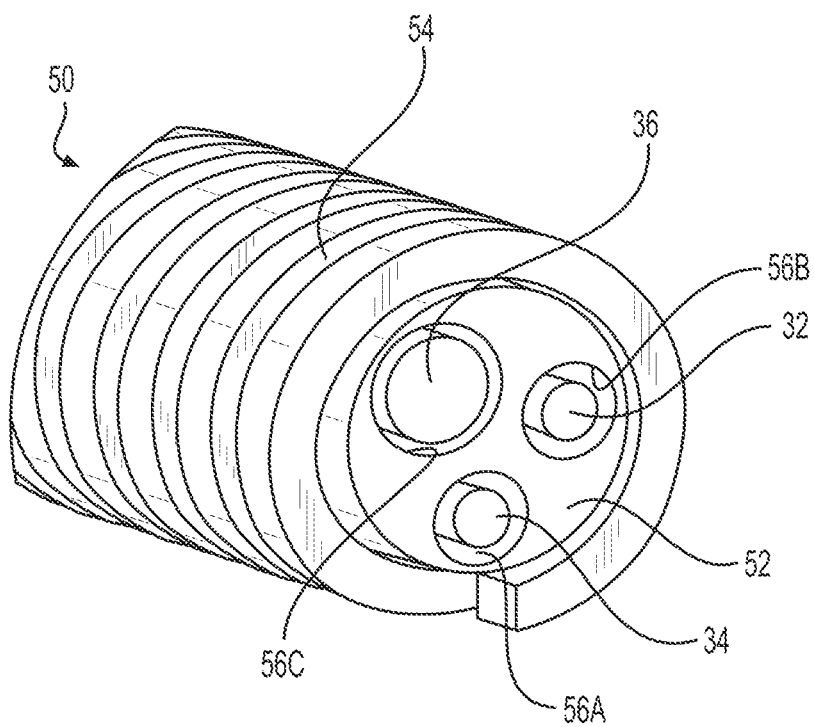
FIGS. 5A-5D illustrate the tubular portion of the medical device of FIG. 2 in different exemplary embodiments.

FIG. 5A illustrates the structure of tubular section 50 in an exemplary embodiment. Tubular section 50 includes a multi-lumen elongate member 52 positioned within a coil

54. Coil 54 may include a stainless steel or another suitable material (e.g., Nitinol, etc.) that provides sufficient stiffness to the tubular section 50. In some embodiments, the coil 54 may include a wire wound around the elongate member 52. In some embodiments, the coil 54 can be used without the multi lumen elongate member 52 and the steering wires 32, 34 and pull wire 36 can be passed through coil 54 as illustrated, for example, in FIG. 5D. In some embodiments, the coil 54 may be attached to the external surface of the elongate member 52, for example, by crimping, adhesive, heat-shrink, etc. The dimensions (thickness, etc.) of the coil 54, and/or its configuration (pitch, etc.), may depend upon the desired stiffness of the tubular section 50. Elongate member 52 may include lumens 56A, 56B, and 56C that extend therethrough. The steering wires 32, 34 and the pull wire 36 may extend from the handle 10 to the distal portion 250 of device 500 through these lumens 56A, 56B, 56C. For example, as illustrated in FIG. 5A, steering wires 32 and 34 may extend through lumens 56A and 56B respectively, and pull wire 36 may extend through lumen 56C. In general, these lumens 56A-56C may be sized larger (e.g., slightly larger) than the wires that extend through the respective lumen so that these lumens impose minimal interference to the wire that passes therethrough. In some embodiments, tube 52 may be made of a lubricious material (such as, for example, PTFE, a Pebax® elastomer, silicone, etc.) to reduce friction between the tube and the wires (steering and pull wires, 32, 34, 36) that pass therethrough.

Figure 5B:
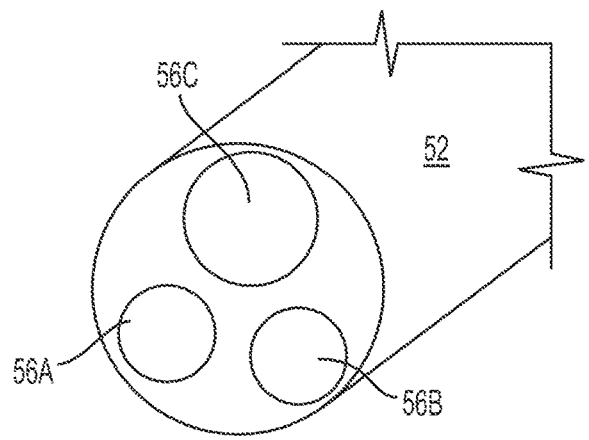
Figure 5C:
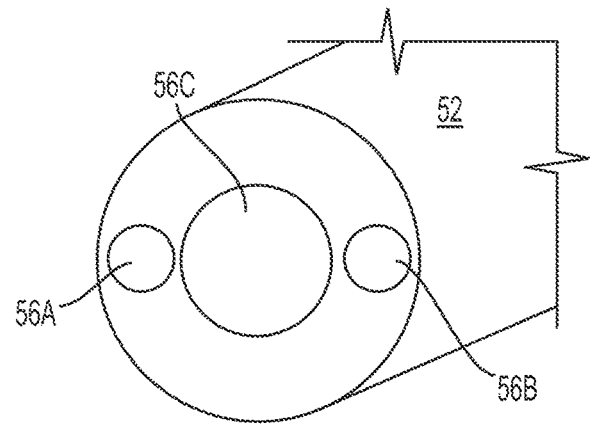
Figure 5D:
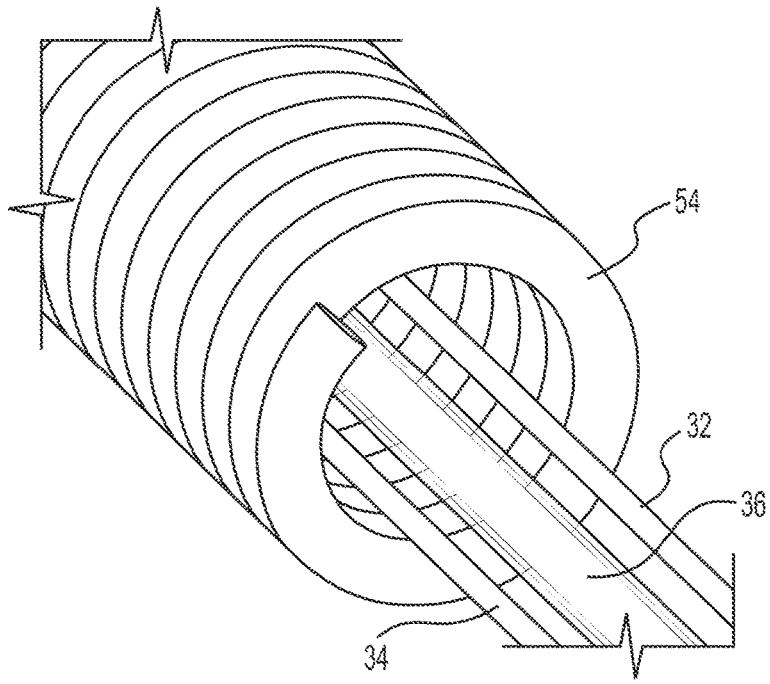

It should be noted that, although FIG. 5A illustrates a particular configuration of lumens 56A-56C in the elongate member 52, this is only exemplary. In general, lumens 56A-56C may be arranged in any configuration in the elongate member 52. FIGS. 5B and 5C illustrate exemplary elongate members 52 with lumens arranged in different configurations. In the embodiment of FIG. 5B, the lumens 56A-56C are arranged in a substantially triangular configuration, and in the embodiment of FIG. 5C, the lumens 56A-56C are arranged in a linear configuration. It should be noted that these configurations are exemplary and other configurations of lumens 56A-56C are possible. It should also be noted that, although lumens 56A and 56B are illustrated as being substantially the same size, and lumen 56C is illustrated as being larger than lumens 56A and 56B, this is only exemplary. In general, these lumens may have any size (same size or different sizes).

Figure 6A:
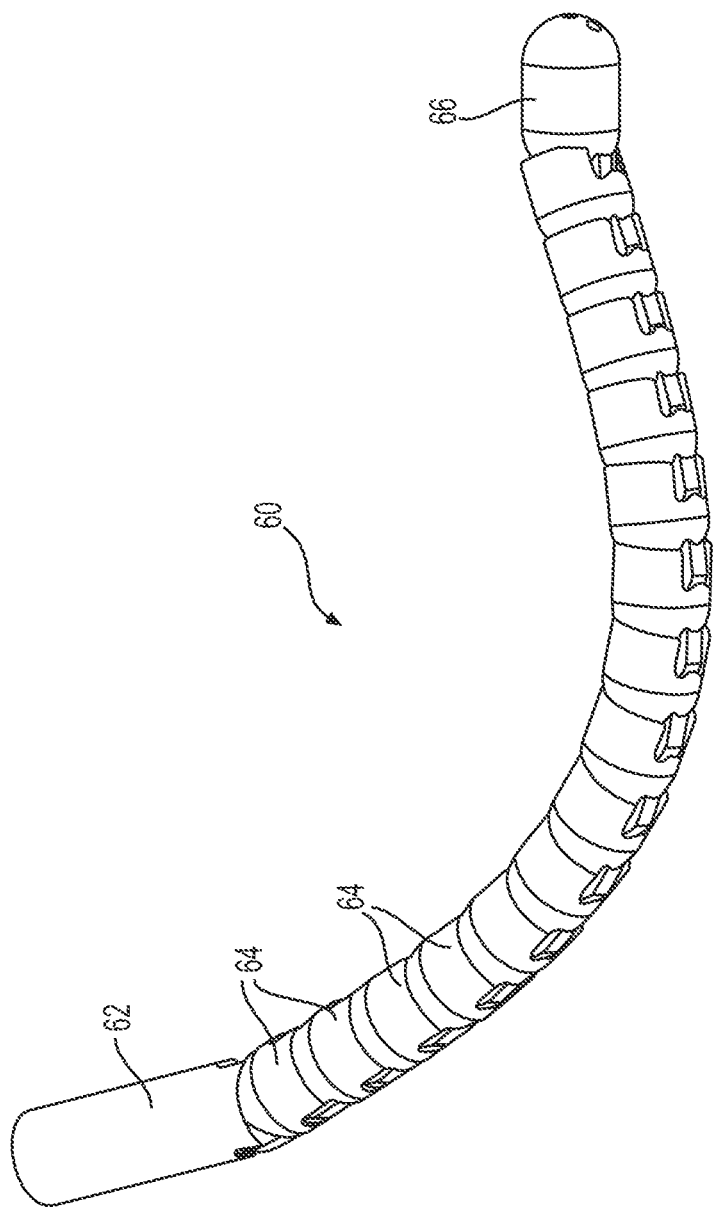

With reference to FIG. 2, at its distal end, tubular section 50 is connected to the articulation region 60 of the distal portion 250. FIGS. 6A-6C illustrate different views of an exemplary embodiment of the articulation region 60. FIG. 6A illustrates a perspective view of the articulation region 60 in a curved configuration, and FIGS. 6B and 6C illustrate side views of the proximal and distal regions, respectively, of the articulation region 60. Articulation region 60 enables the end effector 120 of the medical device 500 to move side-to-side in the YZ plane (see FIGS. 2 and 6C). The articulation region 60 includes a proximal end cap 62, a distal end cap 66, and multiple links 64 positioned between the proximal and distal end caps 62, 66. The multiple links 64 are stacked one over the other and coupled together such that each link 64 can rotate with respect to adjacent links 64. FIGS. 6D and 6E illustrate perspective views of opposite end surfaces of the proximal end cap 62, and FIGS. 6F and 6G illustrate perspective views of opposite ends of a link 64.

As can be seen in FIGS. 6B and 6E, the proximal end of proximal end cap 62 is attached to the distal end of the tubular section 50, and its distal end includes a recess 62D. As best seen in FIGS. 6F and 6G, the distal end of link 64 includes a recess 64D and its proximal end includes a projecting region 64C. The multiple links 64 of articulation region 60 are assembled such that the projecting region 64C of one link 64 is positioned in the recess 64D of an adjoining link 64. The mating surfaces of the projecting regions 64C and the recesses 64D are curved such that each link 64 is configured to rotate about its adjacent link 64. At its proximal end, the projecting region 64C of a link 64 is similarly fit into the recess 62D of the proximal end cap 62 such that this link 64 is configured to rotate about the proximal end cap 62. For example, the top surface 64F of projecting region 64C of link 64 may have a shape and/or curvature that corresponds to the shape and/or curvature of base 62F, 62F" of recess 62D, 64D of proximal end cap 62 and link 64. When the links 64 are assembled with the proximal end cap 62, the curvature of the top surface 64F and base 62F, 62F" enables the links 64 to rotate with respect to each other. The distal end cap 66 is similarly coupled to a link 64 (see FIG. 6C).

Passages 62A, 62B, and 62C pass through the proximal end cap 62 (see FIGS. 6D and 6E), passages 64A, 64B, and 64C pass through each link 64 (see FIGS. 6F and 6G), and passages 66A, 66B, and 66C pass through the distal end cap 66 (see FIG. 6C). The end caps 62, 66 and the links 64 are arranged such that passages 62A, 64A, and 66A are aligned to form an aligned passageway, passages 62B, 64B, and 66B are aligned to form an aligned passageway, and passages 62C, 64C, and 66C are aligned to form an aligned passageway. The two steering wires 32, 34 and the pull wire 36 pass through these aligned passageways of the articulation region 60. For example, steering wire 32 passes through a passageway formed by passages 62A, 64A, and 66A, steering wire 34 passes through a passageway formed by passages 62B, 64B, and 66B, and pull wire 36 passes through a passageway formed by passages 62C, 64C, and 66C.

Figure 7A:
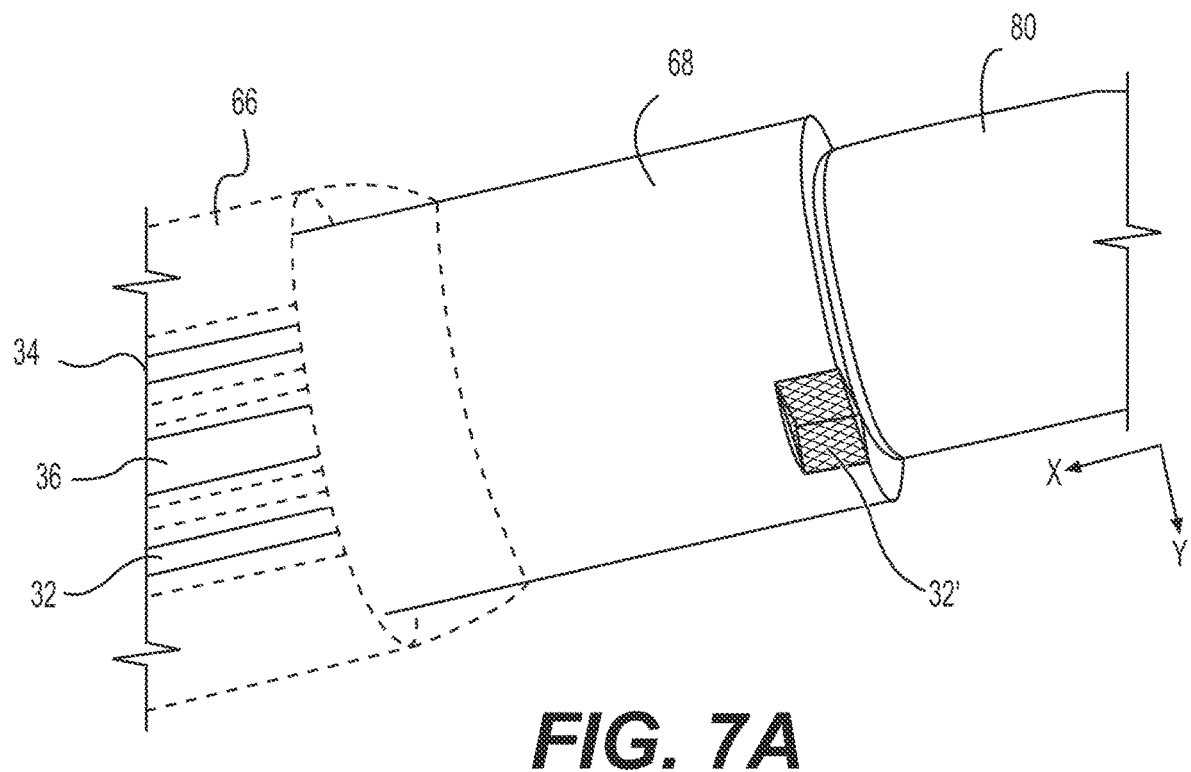
FIGS. 7A-8B illustrate different regions/components of the distal portion of the medical device of FIG. 2.
Figure 7B:
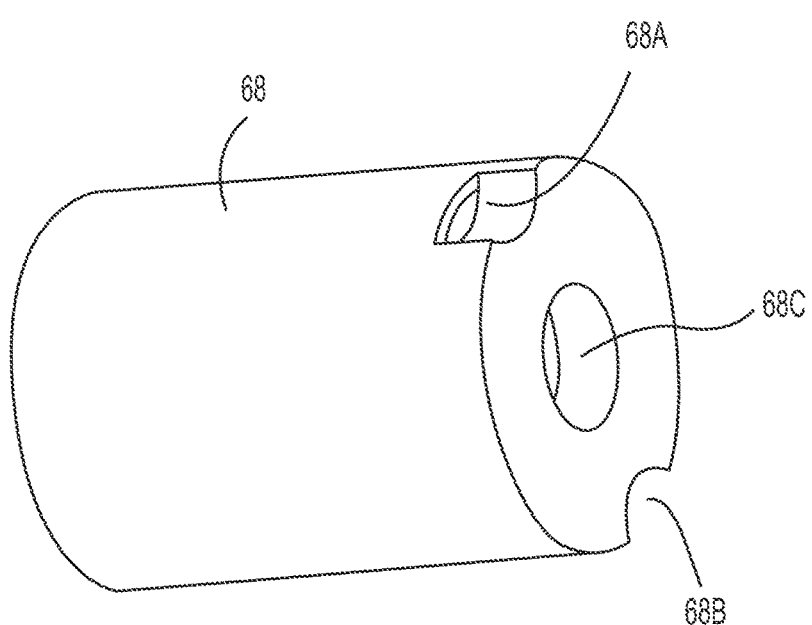

With reference to FIG. 6C, an articulation cap 68 is coupled to the articulation region 60 distal to the distal end cap 66. The steering wires 32 and 34 that pass through the aligned passageways of the articulation region 60 are attached to the articulation cap 68. FIG. 7A illustrates an enlarged view of a region of the distal portion 250 of device 500 showing the articulation cap 68. And, FIG. 7B shows the articulation cap 68 in an exemplary embodiment. Articulation cap 68 also includes passages 68A, 68B, and 68C that are aligned with the aligned passageways of the articulation region 60. The steering wires 32, 34 and the pull wire 36 that extend from the articulation region 60 are directed through these passages 68A, 68B, and 68C. While the pull wire 36 passes through articulation cap 68 via passage 68C, the steering wires 32, 34 are attached to the articulation cap 68. In some embodiments, as illustrated in FIG. 7A, the steering wires 32, 34 may be attached to the articulation cap 68 using crimps (e.g., crimp 32') or welds.

Figure 11E:
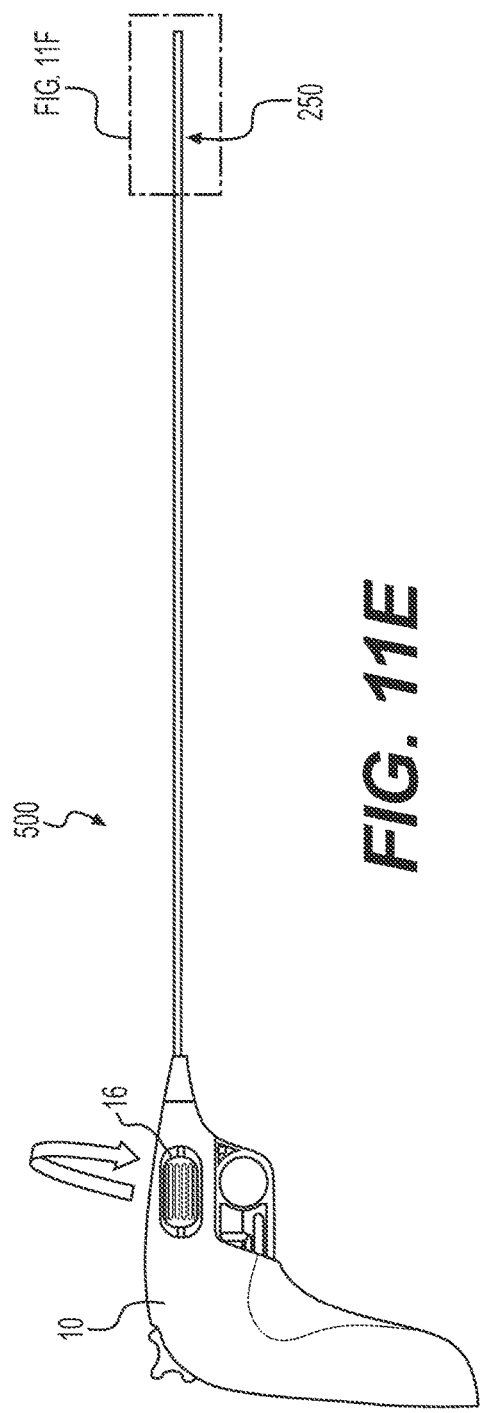
Figure 11F:
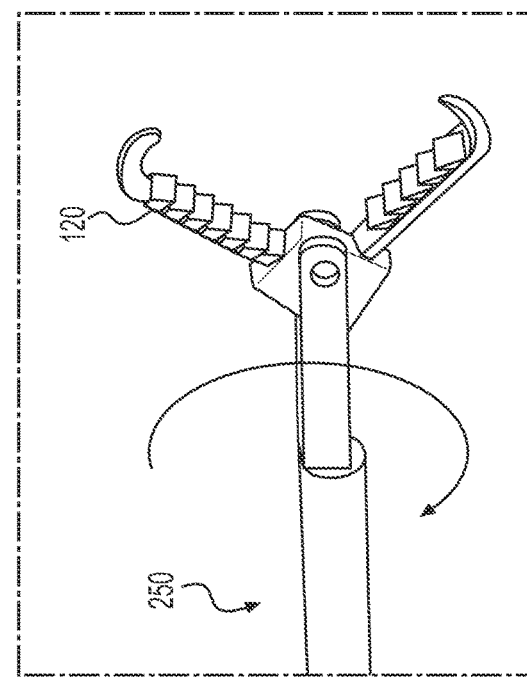

When a tension is applied to one of the steering wires 32, 34 (or a steering wire is pulled) by turning the steering knob 14, the links 64 rotate such that the articulation region 60 bends in the direction of the pulled steering wire. Although not a requirement, in some embodiments, the passageways through which the steering wires 32, 34 pass in the articulation region 60 may be positioned opposite one another (e.g., about 180° apart). For example, as illustrated in FIG. 6C, the steering wires 32 and 34 in the articulation region 60 may be aligned along the Z-axis. In such embodiments, when steering wire 34 is pulled (or a tension is applied to steering wire 34), the articulation region 60 bends towards steering wire 34 and causes the end effector 120 to move in the −Z direction. And, when steering wire 32 is pulled, the articulation region 60 bends towards steering wire 32 and cause the end effector 120 to move in the +Z direction. That is, actuation of the steering knob 14 will cause the end effector 120 to move along the Z-axis. To move the end effector 120 along, for example, the Y-axis, the handle 10 may be rotated by 90° to rotate the tubular section 50 and the articulation region 60 by the same angle, and align the steering wires 32, 34 along the Y-axis. Actuation of the steering knob 14 when the steering wires 32, 34 are aligned along the Y-axis will move the end effector 120 along the Y-axis. In a similar manner, the end effector 120 may be moved in any direction in the YZ plane by rotating the handle 10 to align the steering wires 32, 34 (in the articulation region 60) in the desired direction and actuating the steering knob 14. Note that, since rotation of the tubular section 50 (and articulation region 60) is independent of the rotation of the pull wire 36, when the articulation region 60 is rotated by rotating the handle 10, both the pull wire rotation and tubular section rotation are independent of each other. When handle 10 is rotated, the tubular section rotates along with distal region 250 and end effector 120. When rotating knob 16 is rotated, the pull wire 36 is rotated which rotates only the end effector 120 without rotating the tubular section 50 and distal region 250 as schematically illustrated in FIGS. 11E and 11F.

With reference to FIG. 6C, the pull wire 36 that extends out of the articulation cap 68 passes through a bushing 80 and a clevis 90 and is coupled to the end effector 120, for example, via a four-bar link (or another suitable) mechanism (not shown). As would be recognized by a person skilled in the art, the four-bar link mechanism may be configured to open and close the jaws of the end effector 120 in response to back and forth translation of the pull wire 36 along the X-axis. Since four-bar links and other suitable mechanisms that actuate end effectors in response to translation of a pull wire 36 are known in the art, they are not described herein.

With reference again to FIG. 6C, the end effector 120 is coupled to the clevis 90 at the distal end of the clevis 90. The clevis 90 is coupled to the bushing 80 such that it can rotate on the bushing 80 about the X-axis. Rotation of the clevis 90 on the bushing 80 enables the end effector 120 to rotate along with the pull wire 36 independent of the articulation region 60. That is, when the rotation knob 16 of the handle 10 is turned to rotate the pull wire 36, the end effector 120 that is coupled to the distal end of the pull wire 36 also rotates. The clevis 90, rotatably coupled to the bushing 80, enables the end effector 120 to rotate independent of the actuation region 60 of the device 500.

Figure 8A:
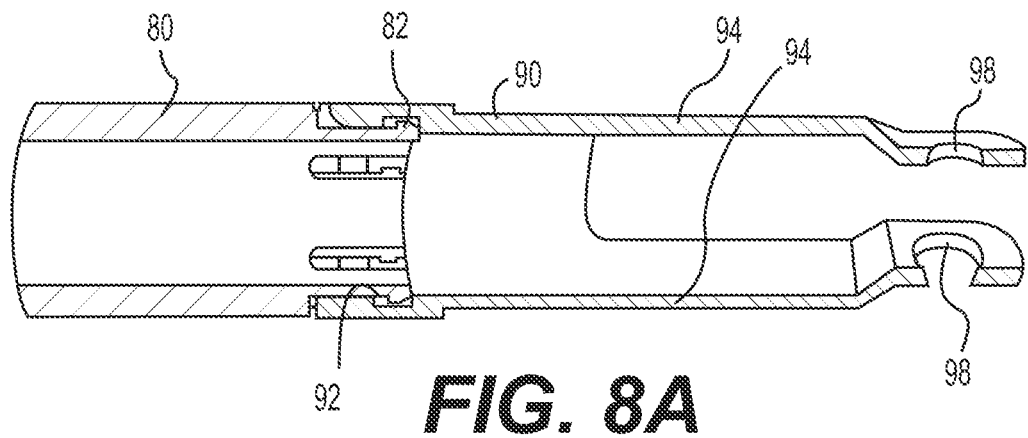

FIG. 8A illustrates a cross-sectional view of the bushing 80 and the clevis 90 coupled together. As can be seen in FIG. 8A, bushing 80 is a substantially cylindrical component with multiple spaced-apart slits at its distal end. The slits reduce the stiffness of the bushing 80 at its distal end and enable the proximal end of the clevis 90 to be fit over the distal end of the bushing 80. A collar 82 is defined at the distal end of the bushing 80. The clevis 90 has a cylindrical region with an undercut 92 (or groove) at its proximal end. The cylindrical proximal end of the clevis 90 is fit over the distal end of the bushing 80 with the bush collar 82 positioned in the clevis undercut 92. The bushing 80 and the clevis 90 are dimensioned to allow the clevis 90 to freely rotate on the bushing 80. The distal end of the clevis 90 includes a pair of flanges 94 (or arms) with cavities 98 extending transversely through its distal end. The jaws of the end effector 120 are coupled to the cavities 98 of the flanges 94.

Figure 8B:
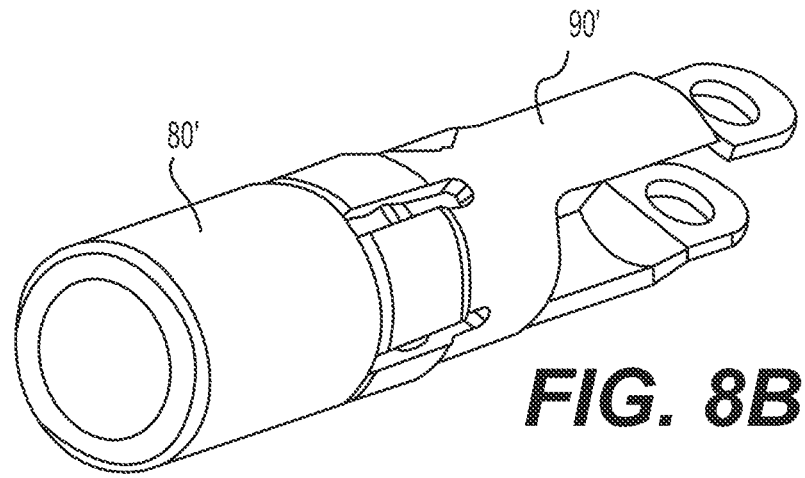

As would be recognized by a person skilled in the art, different embodiments of disclosed medical devices may include many variations of the above described features. For example, in some embodiments, as illustrated in FIG. 8B, the proximal end of a clevis 90' may have slits to decrease its stiffness (or increase its flexibility) and enable the clevis 90' to be fit over the distal end of a bushing 80'.

Figure 9A:
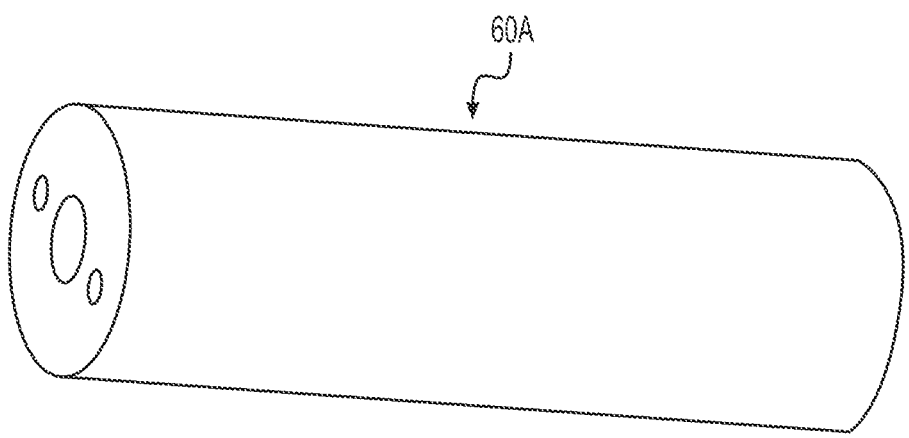
FIGS. 9A-9D illustrate different embodiments of articulation regions that may be used in the medical device of FIG. 2.

In some embodiments, a disclosed medical device may include an articulation region having a configuration different from that described above. FIGS. 9A-9D illustrate different exemplary configurations of articulation regions that may be used in the disclosed medical devices. In some embodiments, as illustrated in FIG. 9A, articulation region 60A of a disclosed medical device 500 may be formed of a flexible material (such as, for example, a Pebax® elastomer, a flexible PTFE, or another biocompatible flexible material). In some embodiments, articulation region 60A may be a cylindrical or substantially cylindrical member with a constant (or substantially constant) outer diameter. As illustrated in FIG. 9A, passages for the steering wires and the push wire may extend longitudinally through the flexible material. As described previously with reference to articulation region 60, steering wires 32, 34 and push wire 36 extend through the respective passages of articulation region 60A. When one of the steering wires 32, 34 is pulled, the flexible articulation region 60A bends in the direction of the pulled steering wire. The resilience of the material used to form the articulation region 60A may be such that the articulation region 60A returns to its original configuration (e.g., linear) when the force on the pulled steering wire is released.

Figure 9B:
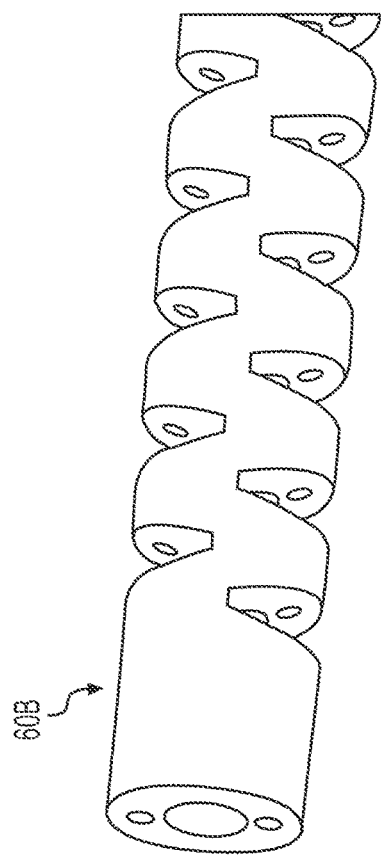

In some embodiments, as illustrated in FIG. 9B, articulation region 60B may be formed by cutting alternate slits in a cylindrical (or substantially cylindrical) member to make it flexible. In some embodiments, the cylindrical member may be formed of a biocompatible metal. However, this is not a requirement. As illustrated in FIG. 9B, the adjacent slits on the articulation region 60B may be spaced apart along the longitudinal axis of the cylindrical member and may face in opposite directions. Longitudinal passages may be formed through the cylindrical member for the steering wires and the push wire. Although slits have a triangular cross-sectional shape are illustrated in FIG. 9B, this is only exemplary. In general, these slits may have any configuration. As in articulation region 60A of FIG. 9A, when one of the steering wires 32, 34 of articulation region 60B is pulled, the flexible articulation region 60B bends in the direction of the pulled steering wire. And, the resilience of the material (used to form articulation region' 60B) may return articulation region 60B to its original configuration (e.g., linear) when the steering wire is released.

Figure 9C:
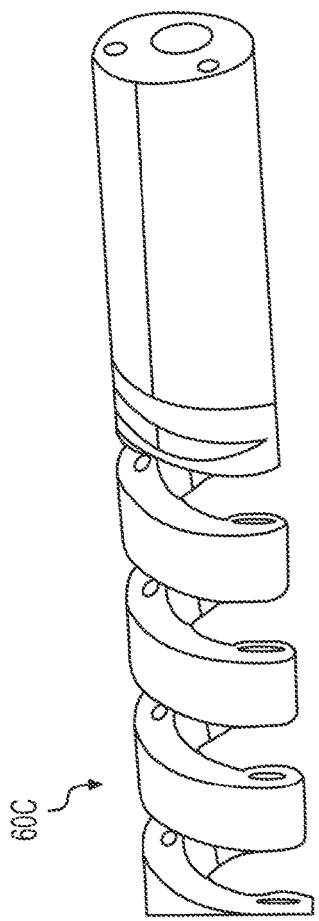
Figure 9D:
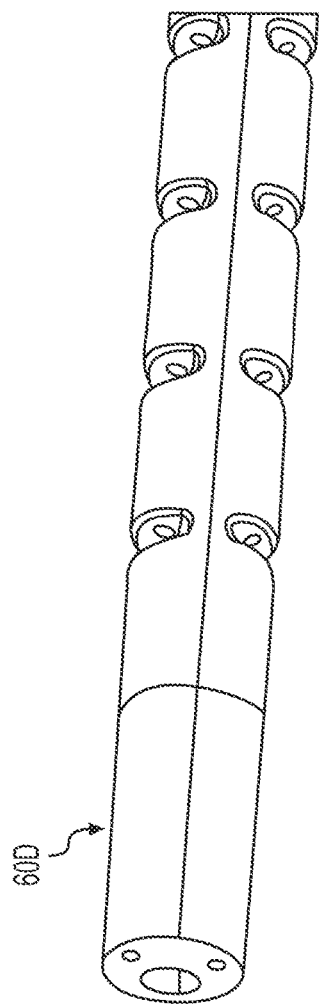

In some embodiments, as illustrated in FIG. 9C, articulation region 60C may have a spiral configuration. In some embodiments, an elongate member having a spiral configuration may be formed (by any process) and end caps having a cylindrical configuration may be attached to the opposite ends of the spiral elongate member (only one end seen in FIG. 9C). In some embodiments, the central section (e.g., the section between two ends) of an elongate member may be machined (or processed in another manner) to have a spiral configuration. The articulation region 60C may be formed of any biocompatible material (e.g., metal, etc.). Passages for the steering wires 32, 34 and the push wire 36 may then be formed longitudinally through the elongate member. In some embodiments, the central passageway of the spiral elongate member may be used for extending the push wire 36, and longitudinal passages may be formed through the spiral member for the steering wires 32, 34. The spiral configuration of the central section of the articulation region 60C may impart flexibility to this section of the articulation region 60C. When one of the steering wires 32, 34 is pulled, the flexible spiral section of articulation region 60C bends in the direction of the pulled steering wire. And, when the pulled steering wire is released, the spiral section returns to its original configuration.

In some embodiments, an articulation region 60D may be formed by providing longitudinally spaced-apart slits or slots through a cylindrical (or substantially cylindrical) member. The cylindrical member may be formed of any biocompatible material, the slots may have any configuration, and the slots may be spaced apart by any distance. In general, the cylindrical member of the articulation region 60D may be flexible. The flexibility may be as a result of the material (used to form the articulation region 60D) and/or as a result of the configuration and spacing of the slots. Longitudinal passageways may be formed through the flexible cylindrical member for the steering wires 32, 34 and the pull wire 36. As in each of articulation regions 60A-60C, the centrally positioned passage may be used to pass the push wire 36 and the smaller passages on either side of the central passage may be used to pass the steering wires 32, 34. And, when one of the steering wires 32, 34 is pulled, the flexible articulation region 60D bends in the direction of the pulled steering wire. And, when the pulled steering wire is released, the articulation region 60D returns to its original configuration.

Figure 10A:
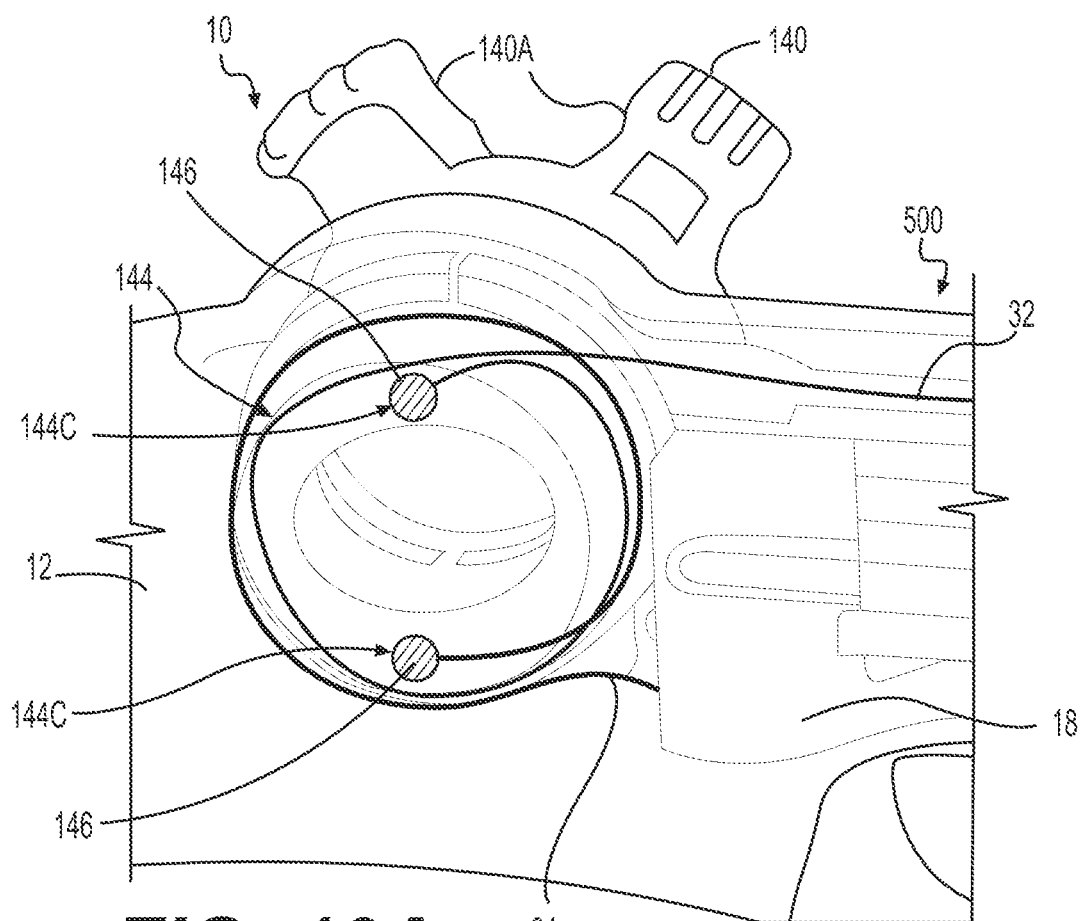
FIGS. 10A-10D illustrate different regions/components of an exemplary steering knob that may be used in the medical device of FIG. 2.
Figure 10B:
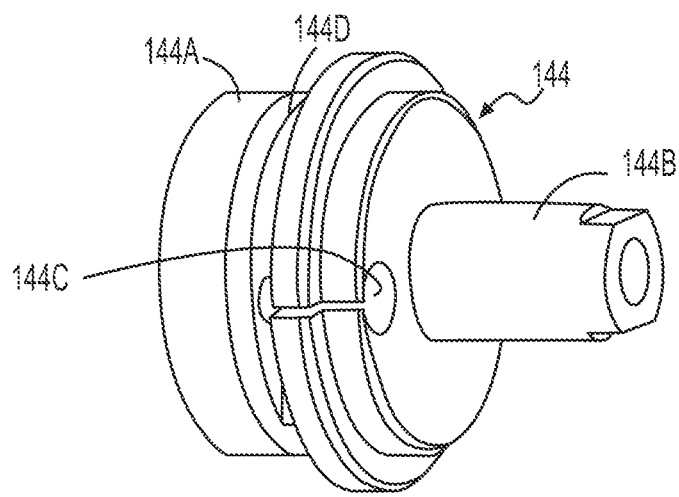
Figure 10C:
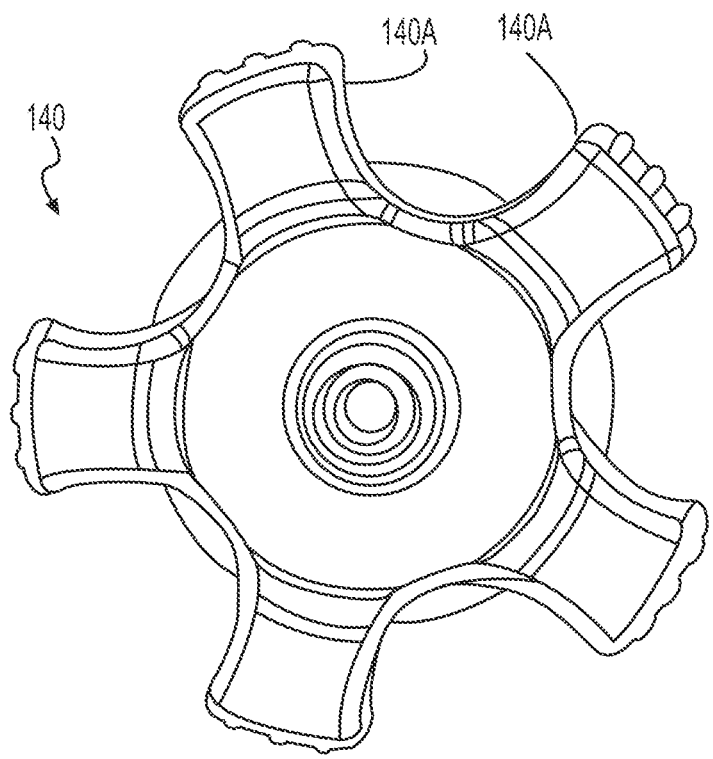
Figure 10D:
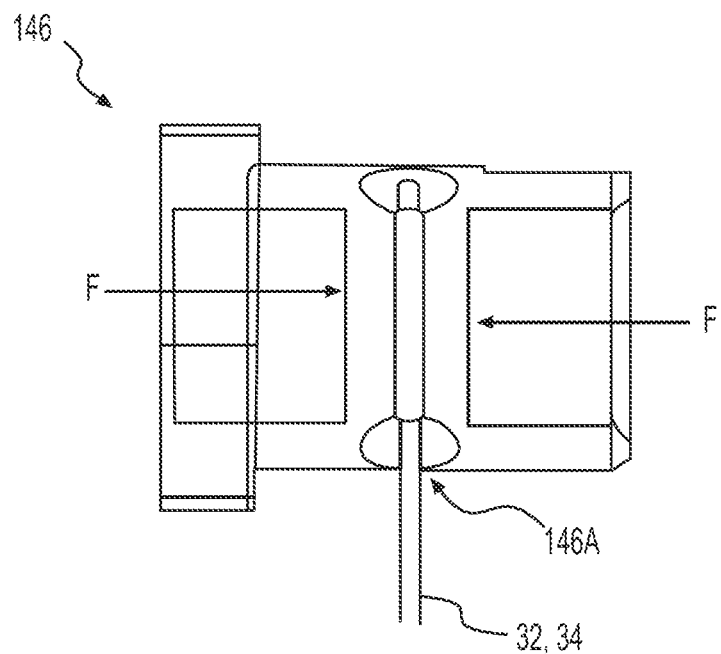

In some embodiments, the steering knob 14, rotation knob 16, and/or the actuation knob 18 may have a configuration different from those described above. FIG. 10A illustrates a medical device 500 employing a different configuration of a steering knob 140. FIG. 10C illustrates steering knob 140 separated from medical device 500. Steering knob 140 includes multiple supports 140A (e.g., thumb supports) for rotation of the steering knob 140. A wire holder 144 (see FIGS. 10A-10B) is coupled to the steering knob 140 such that rotation of the steering knob 140 rotates the wire holder 144. FIG. 10B illustrates the wire holder 144 in an exemplary embodiment. The steering wires 32, 34 of the device 500 are coupled to the wire holder 144. Wire holder 144 includes a disc-like support region 144A with a shaft 144B extending therefrom. The shaft 144B of the support region 144A is coupled to the steering knob 140 (for example, using fasteners, adhesive, friction, etc.). The support region 144A includes features that engage with corresponding features on the proximal end of the steering wires 32, 34 to couple the steering wires 32, 34 to the wire holder 144. These features of support region 144A may include holes or cavities 144C that receive crimps 146 attached to an end (e.g., the proximal end) of the steering wires 32, 34. FIG. 10D is a schematic illustration of an exemplary crimp 146 being attached to an end of a steering wire 32, 34. As illustrated in FIG. 10D, an end of the steering wire 32, 34 is inserted into a cavity 146A of the crimp 146 and one or more transverse forces F are applied to deform surfaces of the crimp 146 and fixedly attach the crimp 146 to the steering wire 32, 34. The crimps 146 are then supported in the cavities 144C, and the steering wires 32, 34 extend to the distal portion 250 of device 500 through passages in the body 12 of handle 10 as described previously.

In some embodiments, as illustrated in FIG. 10A, the proximal end of the steering wires 32, 34 may be wound around the support region 144A of wire holder 144 with the crimps 146 at their proximal-most end supported in cavities 144C. The support region 144A may include channels 144D that receive the wound steering wires 32, 34. In some embodiments, as shown in FIG. 10A, the proximal end of the steering wires 32, 34 may form one loop around the support region 144A. Although not a requirement, winding the proximal end of the steering wires 32, 34 around the support region 144A may reduce the likelihood of kinks developing in these wires 32, 34 during operation. As explained previously, rotation of the steering knob 140 in one direction applies a pulling force (or tension) on one steering wire (e.g., steering wire 32), and rotation of the steering knob 140 in the opposite direction applies a pulling force on the other steering wire (e.g., steering wire 34).

It should be noted that, although exemplary embodiments of medical devices 500 with two steering wires 32, 34 have been described above, this is not a limitation. In general, the devices 500 of this disclosure may include any number (e.g., 1, 3, 4, etc.) of steering wires arranged around its articulation region (60, 60A, etc.). These steering wires may be arranged in any configuration (e.g., angular spacing) around the articulation region. For example, in some embodiments, medical device 500 may only include a single (i.e., one) steering wire. In some embodiments, the single steering wire may be used to bend the articulation region of device 500 in different directions by using the steering wire in conjunction with the rotation of the handle 10. For example, pulling the steering wire when the handle 10 is positioned in a first configuration (e.g., in the configuration illustrated in FIG. 2) may bend the articulation region of device 500 in a first direction (e.g., in the +Y direction). And, rotating the handle 10 (by, for example, 180°) to rotate the articulation region, and then pulling the same steering wire may bend the articulation region in the opposite direction (e.g., in the −Y direction).

In some embodiments, three steering wires may be spaced apart at an angle of about 120° around the articulation region. And, in some embodiments, four steering wires may be spaced apart at an angle of about 90° around the articulation region. These four steering wires may be actuated by the same or different steering knobs. For example, a first pair of oppositely positioned (e.g., spaced 180° apart) steering wires may be attached to and actuated by a first steering knob and a second pair of oppositely positioned steering wires may be attached to and actuated by a second steering knob. Applying a pulling force on one steering wire causes the articulation region to bend in the direction of the pulled steering wire.

As explained above, exemplary medical devices 500 of this disclosure have multiple independent degrees of freedom that are decoupled from each other. Specifically, in various embodiments of device 500, the independent degrees of freedom include (with reference to FIG. 2): (a) the end effector 120 can be actuated (e.g., opened and closed) using the actuation knob 18; (b) the end effector 120 can be moved (e.g., left-right and up-down) in the YZ plane using the steering knob 14; (c) the end effector 120 can be rotated (clockwise and counter clockwise about the X-axis) using the rotation knob 16; (d) the coil or tubular section 50 of device 500 can be rotated (clockwise and counter clockwise about the X-axis) by rotating the handle 10; and (e) the end effector 120 can be moved in the X-direction by moving the handle 10 in the X-direction. And, each of these degrees of freedom is independent and decoupled from each other. During an exemplary medical procedure using a disclosed device 500, the multiple independent degrees of freedom of the device 500 enable its end effector 120 to be manipulated in any desired manner independent of the delivery scope used to introduce the device 500 into the body of a patient.

Figure 11G:
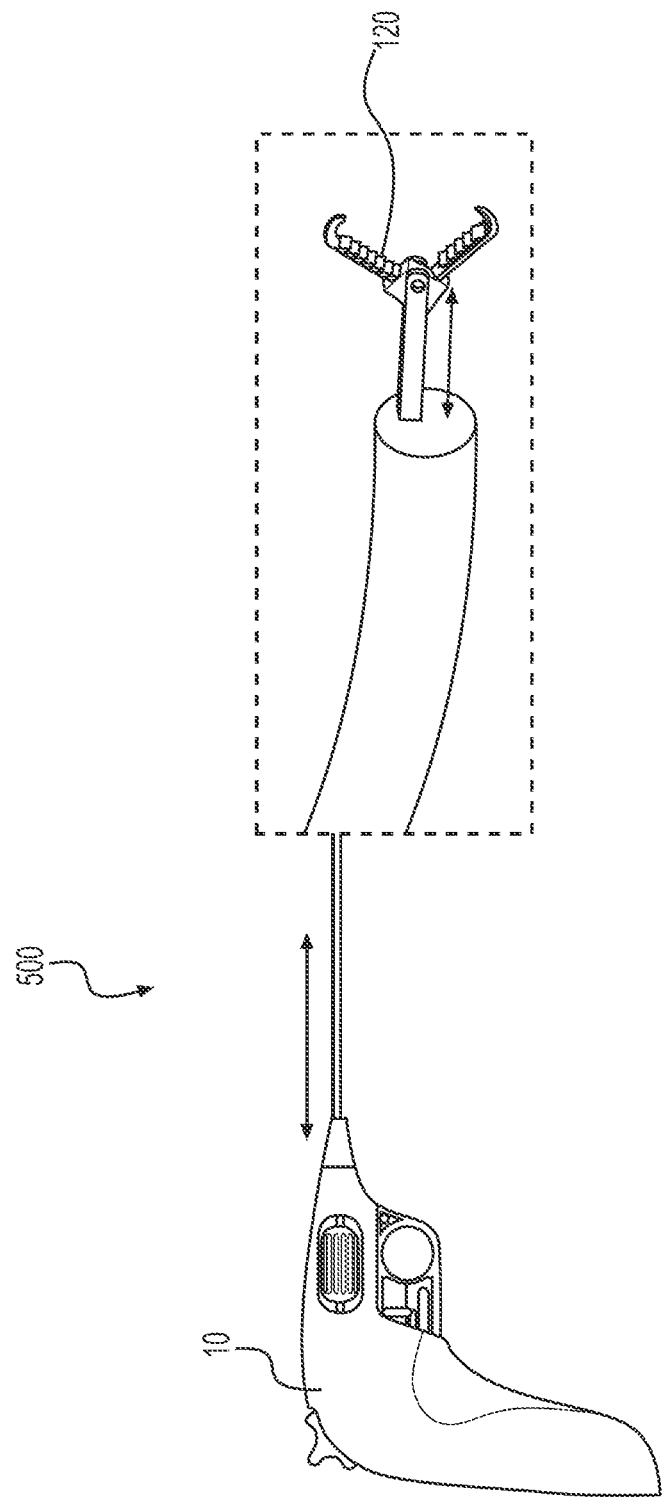

An exemplary medical procedure (e.g., endoscopic mucosal resection) using an exemplary disclosed medical device 500 will now be described. Since such medical procedures are well known in the art, only aspects of the procedure that highlight exemplary features of the disclosed devices will be described below. In the discussion below, reference will be made to FIGS. 1, 2, 3A, and 6C. A delivery scope 1000 (e.g., an endoscope) may be inserted into the patient's body (e.g., into the patient's upper gastrointestinal tract through the mouth) and positioned with its distal end proximate target tissue. Endoscopic medical device 500 may be inserted into the body through a lumen of the delivery scope 1000, and its end effector 120 suitably positioned proximate the target tissue. Initially, the steering wires 32, 34 in articulation region 60 of device 500 may be aligned along, for example, the Y-axis. When in this orientation, the steering knob 14 may be actuated (or turned) to bend the actuation region 60 and move the end effector 120 along the Y-axis. That is, turning the steering knob 14 in one direction will bend the articulation region 60 such that the end effector 120 moves in the +Y direction, and turning the steering knob 14 in the opposite direction will bend the articulation region 60 in the opposite direction such that the end effector 120 moves in the −Y direction. The rotation knob 16 may now be turned to independently rotate the end effector 120. Since rotation of the end effector 120 is decoupled from the rotation of the tubular section 50 and the articulation region 60, operation of the rotation knob 16 rotates the end effector 120 without changing, for example, the bent configuration of the articulation region 60. The handle 10 may be rotated by, for example, 90°, to rotate the articulation region 60 by the same angle, and align the steering wires 32, 34 along the Z-axis. The steering knob 14 may now be actuated to bend the articulation region 60 along the Z-axis, and thereby move the end effector 120 along this axis. At any time during the process, the actuation knob 18 may be activated to open and close the jaws of the end effector 120. The handle 10 can be moved in +/−X direction which will translate the end effector 120 in +/− direction (in-out of endoscope 1000) as schematically illustrated in FIG. 11G.

It should be noted that typical medical procedures using device 500 may include a number of known additional (or alternative) steps that have been omitted in the description above for the sake of brevity. Any above-described step may be omitted or modified, or other steps added, as long as the intended functionality of the disclosed medical devices 500 remains substantially unaltered. Further, although a certain order is described or implied in the described medical procedure, in general, the steps need not be performed in the described order. Further, the described procedure may be incorporated into a more comprehensive medical procedure not described herein.

While principles of this disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
   a handle including an actuation actuator and a rotation actuator;
   an end effector, wherein the actuation actuator is configured to actuate the end effector;
   a tubular section extending between the handle and the end effector, wherein the end effector is configured to be rotated about a first axis extending through the tubular section without rotating the tubular section, and the tubular section is configured to be rotated about the first axis with the end effector; and
   a core wire extending through the tubular section and coupled to the actuation actuator and the end effector, wherein actuation of the actuation actuator causes translation of the core wire in the handle,
   wherein the core wire is rotatably coupled to the actuation actuator, wherein actuation of a rotation actuator rotates the core wire in the actuation actuator,
   wherein a cavity in the rotation actuator accommodates the core wire and has one of a square, a rectangular, a triangular, or a polygonal cross-sectional shape,
   wherein a hypotube is attached to a portion of the core wire extending through the cavity of the rotation actuator, the hypotube having a same cross-sectional shape as the cavity, and
   wherein actuation of the actuation actuator causes the hypotube to translate along with the core wire in the cavity of the rotation actuator.

2. The medical device of claim 1, wherein actuation of the rotation actuator rotates the end effector about the first axis without rotating the tubular section.

3. The medical device of claim 1, wherein the end effector is rotatably coupled to the tubular section such that the end effector is rotatable about the first axis with the tubular section.

4. The medical device of claim 1, further including (a) an articulation region coupled to a distal end of the tubular section and (b) a steering actuator on the handle, wherein actuation of the steering actuator bends the articulation region in a first plane passing through the first axis.

5. The medical device of claim 4, further including one or more steering wires coupled to the steering actuator and extending through the articulation region along the first plane, wherein actuation of the steering actuator applies tension to at least one of the one or more steering wires to bend the articulation region in the first plane.

6. The medical device of claim 5, wherein the articulation region includes multiple links that are rotatably coupled together.

7. The medical device of claim 5, wherein the articulation region includes a flexible elongate member having multiple passages extending longitudinally therethrough.

8. The medical device of claim 5, wherein the one or more steering wires include one steering wire.

9. The medical device of claim 5, wherein the one or more steering wires include two steering wires.

* * * * *